(12) United States Patent
Düx et al.

(10) Patent No.: US 8,952,189 B2
(45) Date of Patent: Feb. 10, 2015

(54) PROCESS FOR PREPARING DIARYL CARBONATES OR ALKYL ARYL CARBONATES FROM DIALKYL CARBONATES

(75) Inventors: Andre Düx, Brühl (DE); Helmut Mothes, Langenfeld (DE); Kaspar Hallenberger, Leverkusen (DE); Georg Ronge, Düsseldorf (DE); Rafael Warsitz, Essen (DE); Pieter Ooms, Krefeld (DE); Johann Rechner, Kempen (DE)

(73) Assignee: Bayer MaterialScience AG (DE)

( * ) Notice: Subject to any disclaimer, the term of this patent is extended or adjusted under 35 U.S.C. 154(b) by 549 days.

(21) Appl. No.: 12/755,873

(22) Filed: Apr. 7, 2010

(65) Prior Publication Data

US 2010/0261928 A1 Oct. 14, 2010

(30) Foreign Application Priority Data

Apr. 8, 2009 (DE) .......................... 10 2009 016 853

(51) Int. Cl.
*C07C 68/06* (2006.01)
*C07C 69/96* (2006.01)

(52) U.S. Cl.
CPC ..................................... *C07C 68/06* (2013.01)
USPC ......................................... 558/270; 558/274

(58) Field of Classification Search
None
See application file for complete search history.

(56) References Cited

U.S. PATENT DOCUMENTS

| | | |
|---|---|---|
| 4,252,737 A | 2/1981 | Krimm et al. |
| 4,330,665 A | 5/1982 | Krimm et al. |
| 4,552,704 A | 11/1985 | Mark |
| 4,554,110 A | 11/1985 | Mark |
| 5,149,856 A | 9/1992 | Schön et al. |
| 5,166,393 A | 11/1992 | Fukuoka et al. |
| 5,334,742 A | 8/1994 | Schön et al. |
| 5,344,954 A | 9/1994 | Schön et al. |
| 5,354,923 A | 10/1994 | Schön et al. |
| 2008/0221348 A1 | 9/2008 | Fukuoka et al. |
| 2009/0076293 A1 | 3/2009 | Dux et al. |

FOREIGN PATENT DOCUMENTS

| | | |
|---|---|---|
| CA | 1242309 A1 | 9/1988 |
| DE | 258412 C | 4/1913 |
| DE | 1767518 A1 | 9/1971 |
| DE | 3445552 A1 | 7/1985 |
| DE | 3445555 A1 | 7/1985 |
| DE | 4006520 A1 | 9/1991 |
| DE | 4036594 A1 | 5/1992 |
| DE | 4226755 A1 | 2/1994 |
| DE | 4226756 A1 | 2/1994 |
| EP | 0000879 A1 | 3/1979 |
| EP | 0000880 A1 | 3/1979 |
| EP | 0039452 A2 | 11/1981 |
| EP | 126288 A2 | 11/1984 |
| EP | 0461274 A1 | 12/1991 |
| EP | 0781760 A1 | 7/1997 |
| EP | 1762559 A1 | 3/2007 |
| EP | 1762560 A1 | 3/2007 |
| EP | 1767516 A1 | 3/2007 |
| EP | 1767517 A1 | 3/2007 |
| EP | 1775280 A1 | 4/2007 |
| EP | 2036880 A2 | 3/2009 |
| GB | 25338 A | 0/1912 |
| GB | 1199953 A | 7/1970 |
| JP | 54-125617 A | 9/1979 |
| JP | 57-176932 A | 10/1982 |
| JP | 61-172852 A | 8/1986 |
| JP | 64-5588 B | 1/1989 |
| JP | 01-093560 A | 4/1989 |
| JP | 01-093580 A | 4/1989 |
| JP | 2004/075570 | 11/2004 |
| WO | WO-2006/001256 A1 | 1/2006 |
| WO | WO-2006/033291 A1 | 3/2006 |

OTHER PUBLICATIONS

Agrawal et al. (Ind. Eng. Chem. Res. 1996, 35, pp. 2801-2807).*
Machine translation of JP 2004-075570. Obtained from <http://dossier.ipdl.inpit.go.jp/text_trans.html> Accessed May 22, 2012.*
"Reactive Distillation," Carl von Ossietzky Oldenburg University; Aug. 26, 2004. Accessed Sep. 20, 2013. <http://www.gmehling.chemie.uni-oldenburg.de/9694.html>.*
Mueller et al., "Reactive Distillation in a Dividing Wall Column: Rate-Based Modeling and Simulation", *Ind. Eng. Chem. Res.*, vol. 46, pp. 3709-3719 (2007).

* cited by examiner

*Primary Examiner* — Kamal Saeed
(74) *Attorney, Agent, or Firm* — Drinker Biddle & Reath LLP

(57) ABSTRACT

The invention relates to a process for preparing diaryl carbonates and/or alkyl aryl carbonates from dialkyl carbonates and aromatic hydroxy compounds using a reactive dividing wall column.

16 Claims, 9 Drawing Sheets

PROCESS FOR PREPARING DIARYL CARBONATES OR ALKYL ARYL CARBONATES FROM DIALKYL CARBONATES

RELATED APPLICATIONS

This application claims benefit to German Patent Application No. 10 2009 016 853.2, filed Apr. 8, 2009, which is incorporated herein by reference in its entirety for all useful purposes.

BACKGROUND OF THE INVENTION

The invention relates to a process for preparing diaryl carbonates and/or alkyl aryl carbonates from dialkyl carbonates and aromatic hydroxy compounds using a reactive dividing wall column.

The preparation of aromatic and aliphatic-aromatic carbonic esters (carbonates) by transesterification starting from aliphatic carbonic esters and aromatic hydroxy compounds is known in principle. This is an equilibrium reaction in which the position of the equilibrium is shifted virtually completely in the direction of the aliphatically substituted carbonates. It is therefore relatively easy to prepare aliphatic carbonates from aromatic carbonates and alcohols. However, to carry out the reaction in the converse sense in the direction of aromatic carbonates, it is necessary to shift the very unfavourable equilibrium effectively to the side of the aromatic carbonates, for which not only very active catalysts but also suitable process conditions have to be employed.

It is known that such equilibrium reactions can be carried out in columns and can in this way be shifted advantageously in the direction of formation of the desired product, as described, for example, by U. Block, Chem.-Ing. Techn. 49, 151 (1977), DE-A 38 09 417, B. Schleper, B. Gutsche, J. Wnuck and L. Jeromin, Chem.-Ing.-Techn. 62, 226 (1990), Ullmans Encyclopädie der technischen Chemie, 4th Edition, Vol. 3; p. 375 ff. 1973).

In the known processes, the transesterification is therefore preferably carried out continuously in a countercurrent transesterification in one or more reaction columns.

However, the processes known from the literature (e.g. EP 0 461 274, DE-A 42 26 755, DE-A 42 26 756) usually describe only those process steps in which the reaction to form diaryl carbonate by transesterification and/or disproportionation takes place. Current patent applications, for example WO 2006/033291 A1, EP 1 775 280A1, EP 1 767 516 A1, EP 1 767 517 A1, EP 1767 518 A1, EP 1 762 559 A1 and EP 1 762 560 A1, also give information regarding the physical designs of reaction columns for preparing diaryl carbonates. The mixtures of reaction alcohol and dialkyl carbonate which are formed in this process are separated in apparatuses separate from the reaction apparatuses.

To improve the economics of the process compared to the prior art, both approaches for reducing the energy consumption and measures for reducing the capital costs are required. On the basis of experience, the two requirements can be fulfilled only with restrictions in industrial practice.

EP-A 0 461 274 describes a continuous transesterification process for preparing aromatic carbonates in one or more multistage columns connected in series, with dialkyl carbonates or alkyl aryl carbonates being reacted with phenols and the volatile products, namely the reaction alcohols and dialkyl carbonates being taken off at the top of the columns and the high-boiling products such as diaryl carbonates being taken off at the bottom of the columns. Since both dialkyl carbonates and the reaction alcohols are taken off at the top of the column, at least one further step is required to separate these components.

DE-A 42 26 756 describes a two-stage process for preparing diaryl carbonates by transesterification of a dialkyl carbonate by means of an aromatic hydroxy compound, in which the corresponding alkyl aryl carbonate is firstly formed from the starting materials in a first stage and the diaryl carbonate is formed in a second stage. The information given in the process description is restricted to the reaction conditions, the catalyst used and the design of the reaction columns. In the case of this patent application, too, reaction alcohol and dialkyl carbonate are taken off at the top of the columns.

DE-A 42 26 755 describes a process for preparing diaryl carbonates in two reaction columns which are coupled with one another in terms of energy and material, in which an aromatic hydroxy compound and a dialkyl carbonate are reacted in the first stage and the alkyl aryl carbonate formed is converted into diaryl carbonate in the second stage either by transesterification with the aromatic hydroxy compound or by disproportionation. However, this has the problem that the integration of the process in terms of material and energy does not allow the reaction conditions to be selected optimally for the formation of the alkyl aryl carbonate or diaryl carbonate since these are fixed by the virtually identical pressures prevailing in the two steps.

EP-A 781 760 describes a continuous process for preparing aromatic carbonates by reaction of a dialkyl carbonate with an aromatic hydroxy compound in the presence of a catalyst, continuous removal of the aromatic carbonate formed in the reaction, the alcoholic by-products, the dialkyl carbonate and the aromatic hydroxy compound, with the dialkyl carbonate and the aromatic hydroxy compound being recirculated to the reaction. In this process, too, only two fractions which are taken off at the upper end and at the bottom, respectively, of the reactor are obtained in the reaction part of the process.

WO-A 2006/001256 describes a process in which an aromatic hydroxy compound is reacted with a dialkyl carbonate in the presence of a catalyst and also an industrial apparatus suitable for this purpose. Here too, the fractions are taken off only as overhead product or bottom product.

Without appropriately efficient integration into terms of apparatus and energy, the capital and energy costs of the above-described processes are, as is known, high, which in turn makes the advantages of the phosgene-free preparation of aryl carbonates questionable from an ecological and economic point of view.

Approaches for integration in terms of apparatus and energy comprise the use of dividing wall columns.

An example of the mode of operation of dividing wall columns in reactive separation processes is described in EP 0 126 288B1. However, no information as to how this technology can be applied in the preparation of diaryl carbonates by transesterification of a dialkyl carbonate is given here.

A further example of a reactive separation process may be found in Ind. Eng. Chem. Res. 2007, 46, 3709-3719. This disclosure describes a transesterification of dimethyl carbonate with ethanol to form the aliphatic diethyl carbonate. Thus, no diaryl carbonate is produced in this process either.

In the transesterification of an aromatic hydroxy compound with an alkyl carbonate, the latter is generally employed in excess in order to achieve a high conversion based on the aromatic hydroxy compound.

In the case of a transesterification in a reaction column, both the dialkyl carbonate used in excess and the reaction alcohol formed in the reaction are separated off at the top of the column. The aromatic hydroxy compound, the alkyl aryl carbonate formed in the reaction, possibly diaryl carbonate and dialkyl carbonate are preferably present in the bottom product. In the case of a homogeneously catalyzed reaction, the bottom product also contains the catalyst.

A disadvantage of this mode of operation is that the dialkyl carbonate used in excess has to be separated from the reaction alcohol in a separate step.

Although a separation of reaction alcohol from the dialkyl carbonate in an enrichment section above the reaction zone is possible in principle, it is relatively ineffective in terms of the conversion since it is thus only introduced from the top into the reaction zone. In this way, only the separation of dialkyl carbonate and aromatic hydroxy compound is increased. However, this effect should be avoided in order to be able to ensure a high conversion of aromatic hydroxy compound.

There is therefore a continuing need to provide a process for preparing aromatic carbonates, i.e. diaryl carbonates and/or alkyl aryl carbonates, preferably diaryl carbonates, which does not have the abovementioned disadvantages and in which a process which is integrated in terms of energy and apparatus compared to the abovementioned known processes is provided.

The object of the invention was accordingly to provide a process for preparing aromatic carbonates, i.e. diaryl carbonates and/or alkyl aryl carbonates, in which, compared to known processes, the reaction of the dialkyl carbonate with the aromatic hydroxy compound and the separation of the mixture of reaction alcohol and dialkyl carbonate by distillation are coupled in terms of apparatus and energy.

EMBODIMENTS OF THE INVENTION

Figure 1:
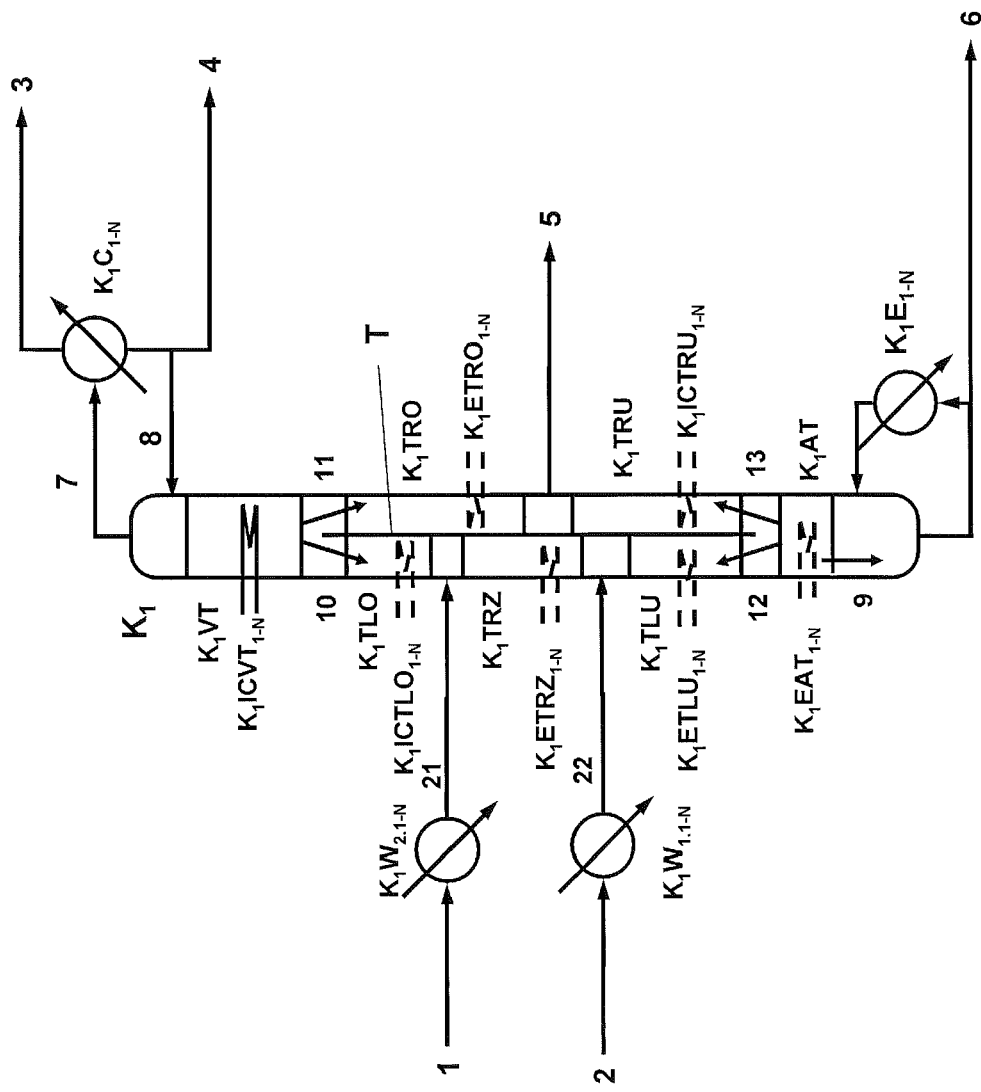
FIG. 1 generally depicts a first transesterification step by means of a reactive dividing wall column.

An embodiment of the present invention is a process for preparing an alkyl aryl carbonate and/or a diaryl carbonate comprising reacting a diallyl carbonate and an aromatic hydroxy compound in the presence of a catalyst in a reactive distillation column, wherein said reactive distillation column is divided by one or more separation devices which are effective in the longitudinal direction and completely or partially prevent transverse mixing of liquid and/or vapour streams into a feed side (Z) in which a reaction zone is located and an offtake side (E), wherein a stream (21) comprising said aromatic hydroxy compound and a stream (22) comprising said dialkyl carbonate are fed to said feed side (Z) and at the same time one or more middle-boiling fractions which optionally comprise reactants and/or reaction products are removed in gaseous or liquid form from the offtake side (E).

Another embodiment of the present invention is the above process, wherein said one or more separation devices completely prevent transverse mixing of liquid and/or vapour streams.

Another embodiment of the present invention is the above process, wherein said stream (21) is fed above said reaction zone and stream (22) is fed below said reaction zone.

Another embodiment of the present invention is the above process, wherein said aromatic hydroxy compound is phenol, said dialkyl carbonate is dimethyl carbonate or diethyl carbonate, and said diaryl carbonate is diphenyl carbonate.

Another embodiment of the present invention is the above process, wherein said reaction is homogeneously catalyzed.

Another embodiment of the present invention is the above process, wherein said stream (21) comprises said catalyst.

Another embodiment of the present invention is the above process, wherein said stream (21) and/or said stream (22) containing the dialkyl carbonate are fed in gaseous or heated form.

Another embodiment of the present invention is the above process, wherein said stream (21) is introduced in liquid form or with only a small proportion of vapour and said stream (22) is fed in gaseous or superheated form.

Another embodiment of the present invention is the above process, wherein at least one further section (K1TLO) which comprises no catalyst or a maximum of 1% by weight of catalyst is present on the feed side (Z) above said reaction zone.

Another embodiment of the present invention is the above process, wherein said section K1TLO is equipped with at least one intermediate condenser and the heat of condensation obtained by condensation in said condenser is returned either directly or indirectly to the process.

Another embodiment of the present invention is the above process, wherein at least one further section (K1TLU) is present on the feed side (Z) below the reaction zone.

Another embodiment of the present invention is the above process, wherein said section K1TLU is equipped with at least one intermediate condenser.

Another embodiment of the present invention is the above process, wherein said at least one intermediate condenser is integrated into said reactive distillation column or present as a separate intermediate condenser outside said reactive distillation column.

Another embodiment of the present invention is the above process, wherein said at least one intermediate condenser is integrated into said reactive distillation column or present as a separate intermediate condenser outside said reactive distillation column.

Another embodiment of the present invention is the above process, wherein said reaction is carried out at a temperature in the range of from 100 to 300° C. and a pressure in the range of from 0.5 to 20 bar.

Another embodiment of the present invention is the above process, wherein the distillate coming from the enrichment section (K1VT) is partly or completely introduced as runback into the column, with the reflux ratio being from 0.5 to 50.

DESCRIPTION OF THE INVENTION

It has now been found that the separation of the reaction alcohol formed in the reaction and the dialkyl carbonate used in excess can be carried out in a reaction column without having to accept the abovementioned disadvantages.

This is surprisingly achieved using a reactive dividing wall column (RDWC).

The invention accordingly provides a process for preparing alkyl aryl carbonates and/or diaryl carbonates from dialkyl carbonates and aromatic hydroxy compounds in the presence of a catalyst by means of a reactive distillation column which is divided by separation devices which are effective in the longitudinal direction and entirely or partially prevent transverse mixing of liquid and/or vapour streams into a feed side (Z) in which a reaction zone is located and an offtake side (E), characterized in that a stream (21) containing the aromatic hydroxy compound and a stream (22) containing the dialkyl carbonate are fed to the feed side and at the same time one or more middle-boiling fractions which can comprise reactants and/or reaction products are taken off in gaseous or liquid form from the offtake side.

The structure of such a reactive dividing wall column is shown in FIG. 1.

The column ($K_1$) is divided into a feed side and an offtake side above the stripping section ($K_1AT$) and below an enrichment section ($K_1VT$) by a dividing wall (T) running in the longitudinal direction.

On the feed side, there is a reaction zone ($K_1TRZ$). In a preferred embodiment, a stream (21) containing the aromatic hydroxy compound and optionally the transesterification catalyst is fed in above this reaction zone and a stream (22) containing the dialkyl carbonate is fed in below the reaction zone, preferably in vapour or heated form.

The stream containing the aromatic hydroxy compound and optionally the catalyst is preferably fed in in liquid form or with only a small proportion of vapour, with the proportion of gas preferably being less than 20% by weight.

The stream containing dialkyl carbonate is preferably introduced in gaseous or superheated form. In preferred embodiments, the superheating of the vapour stream can be from 0 to 50° C.

Diaryl carbonates prepared according to the invention are preferably diaryl carbonates of the general formula (I)

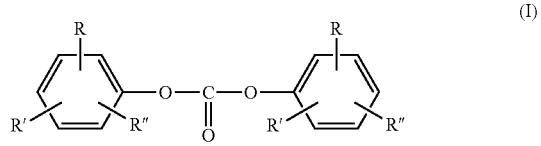

(I)

where R, R' and R" are each, independently of one another, H, linear or branched, optionally substituted $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_6$-alkoxy, particularly preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on the two sides of the formula (I) can be identical or different. R can also be —COO—R''' where R''' can be H, optionally branched $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_6$-alkoxy, particularly preferably $C_1$-$C_4$-alkoxy, $C_5$-$C_{34}$-cycloalkyl, $C_7$-$C_{34}$-alkylaryl or $C_6$-$C_{34}$-aryl. Preference is given to R, R' and R" on the two sides of the formula (I) being identical. R, R' and R" are very particularly preferably H.

Examples of diaryl carbonates of the general formula (I) are: diphenyl carbonate, methylphenyl phenyl carbonates and di(methylphenyl)carbonates, also as a mixture, where the methyl group can be in any position on the phenyl rings, and also dimethylphenyl phenyl carbonates and di(dimethylphenyl)carbonates, also as a mixture, where the methyl groups can be in any positions on the phenyl rings, chlorophenyl phenyl carbonates and di(chlorophenyl)carbonates, where the methyl group can be in any position on the phenyl rings, 4-ethylphenyl phenyl carbonate, di(4-ethylphenyl)carbonate, 4-n-propylphenyl phenyl carbonate, di(4-n-propylphenyl) carbonate, 4-isopropylphenyl phenyl carbonate, di(4-isopropylphenyl)carbonate, 4-n-butylphenyl phenyl carbonate, di(4-n-butylphenyl) carbonate, 4-isobutylphenyl phenyl carbonate, di(4-isobutylphenyl)carbonate, 4-tert-butylphenyl phenyl carbonate, di(4-tert-butylphenyl)carbonate, 4-n-pentylphenyl phenyl carbonate, di(4-n-pentylphenyl)carbonate, 4-n-hexylphenyl phenyl carbonate, di(4-n-hexylphenyl) carbonate, 4-isooctylphenyl phenyl carbonate, di(4-isooctylphenyl)carbonate, 4-n-nonylphenyl phenyl carbonate, di(4-n-nonylphenyl)carbonate, 4-cyclohexylphenyl phenyl carbonate, di(4-cyclohexylphenyl)carbonate, 4-(1-methyl-1-phenylethyl)phenyl phenyl carbonate, di[4-(1-methyl-1-phenylethyl)phenyl]carbonate, biphenyl-4-yl phenyl carbonate, di(biphenyl-4-yl)carbonate, 1-naphthyl phenyl carbonate, 2-naphthyl phenyl carbonate, di(1-naphthyl)carbonate, di(2-naphthyl)carbonate, 4(1-naphthyl)phenyl phenyl carbonate, 4(2-naphthyl)phenyl phenyl carbonate, di[4-(1-naphthyl)phenyl]carbonate, di[4-(2-naphthyl)phenyl]carbonate, 4-phenoxyphenyl phenyl carbonate, di(4-phenoxyphenyl) carbonate, 3-pentadecylphenyl phenyl carbonate, di(3-pentadecylphenyl)carbonate, 4-tritylphenyl phenyl carbonate, di(4-tritylphenyl)carbonate, methylsalicylato phenyl carbonate, di(methylsalicylato) carbonate, ethylsalicylato phenyl carbonate, di(ethylsalicylato) carbonate, n-propylsalicylato phenyl carbonate, di(n-propylsalicylato) carbonate, isopropylsalicylato phenyl carbonate, di(isopropylsalicylato) carbonate, n-butylsalicylato phenyl carbonate, di(n-butylsalicylato)carbonate, isobutylsalicylato phenyl carbonate, di(isobutylsalicylato) carbonate, tert-butylsalicylato phenyl carbonate, di(tert-butylsalicylato) carbonate, di(phenylsalicylato) carbonate and di(benzylsalicylato) carbonate.

Preferred diaryl carbonates are: diphenyl carbonate, 4-tert-butylphenyl phenyl carbonate, di(4-tert-butylphenyl)carbonate, biphenyl-4-yl phenyl carbonate, di(biphenyl-4-yl) carbonate, 4-(1-methyl-1-phenylethyl)phenyl phenyl carbonate and di[4-(1-methyl-1-phenylethyl)phenyl]carbonate.

Particular preference is given to diphenyl carbonate.

Dialkyl carbonates which are preferably used for the purposes of the invention are dialkyl carbonates of the formula (II)

(II)

where $R^1$ and $R^2$ are each, independently of one another, linear or branched, optionally substituted $C_1$-$C_{34}$-alkyl, preferably $C_1$-$C_6$-alkyl, particularly preferably $C_1$-$C_4$-alkyl. $R^1$ and $R^2$ can be identical or different. Preference is given to $R^1$ and $R^2$ being identical.

Preferred dialkyl carbonates are dimethyl carbonate, diethyl carbonate, di(n-propyl)carbonate, di(isopropyl)carbonate, di(n-butyl)carbonate, di(sec-butyl)carbonate, di(tert-butyl)carbonate and dihexyl carbonate. Particular preference is given to dimethyl carbonate or diethyl carbonate. Very particular preference is given to dimethyl carbonate.

Aromatic hydroxy compounds which are suitable for the purposes of the invention are preferably aromatic hydroxy compounds of the general formula (III)

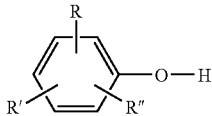

(III)

where R, R' and R" can have, independently of one another, the meanings given for the general formula (I).

Examples of such aromatic hydroxy compounds are: phenol, o-, m- or p-cresol, also as a mixture of cresols, dimethylphenol, also as a mixture, where the methyl groups can be in any positions on the phenol ring, e.g. 2,4-, 2,6- or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicylic acid, isopropylsalicylic acid, n-butylsalicylic acid, isobutylsalicylic acid, tert-butylsalicylic acid, phenylsalicylic acid and benzylsalicylic acid.

Preferred aromatic hydroxy compounds are phenol, 4-tert-butylphenol, biphenyl-4-ol and 4-(1-methyl-1-phenylethyl)phenol.

Particular preference is given to phenol.

Alkyl aryl carbonates prepared according to the invention are preferably alkyl aryl carbonates of the general formula (IV)

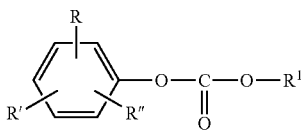

where R, R' and R" can have the meanings given for the general formula (I) and $R^1$ can have the meanings given for the general formula (II).

Preferred alkyl aryl carbonates are methyl phenyl carbonate, ethyl phenyl carbonate, propyl phenyl carbonate, butyl phenyl carbonate and hexyl phenyl carbonate, methyl o-cresyl carbonate, methyl p-cresyl carbonate, ethyl o-cresyl carbonate, ethyl p-cresyl carbonate, methyl or ethyl p-chlorophenyl carbonate. Particularly preferred alkyl aryl carbonates are methyl phenyl carbonate and ethyl phenyl carbonate. Very particular preference is given to methyl phenyl carbonate.

Both the dialkyl carbonates which are suitable for the process of the invention and the aromatic hydroxy compounds are known to those skilled in the art and are commercially available or can be prepared by methods which are likewise known to those skilled in the art.

For the purposes of the invention, $C_1$-$C_4$-alkyl is, for example, methyl, ethyl, n-propyl, isopropyl, n-butyl, sec-butyl, tert-butyl, and $C_1$-$C_6$-alkyl can also be, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, and $C_1$-$C_{34}$-alkyl can also be, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical in, for example, aralkyl or alkylaryl radicals. Alkylene radicals in the corresponding hydroxyalkyl or aralkyl or alkylaryl radicals are, for example, the alkylene radicals corresponding to the above alkyl radicals.

Aryl is a carbocyclic aromatic radical having from 6 to 34 skeletal carbon atoms. The same applies to the aromatic part of an arylalkyl radical, also referred to as an aralkyl radical, and to aryl constituents of more complex groups, e.g. arylcarbonyl radicals.

Arylalkyl or aralkyl is in each case independently, a straight-chain, cyclic, branched or unbranched alkyl radical as defined above which may be monosubstituted, polysubstituted or persubstituted by aryl radicals as defined above.

The above listings are by way of example and are not to be construed as a limitation.

In the process of the invention, the aromatic hydroxy compound(s) and the dialkyl carbonate(s) are preferably used in a molar ratio of from 1:0.1 to 1:10, particularly preferably from 1:0.2 to 1:5, very particularly preferably from 1:0.5 to 1:3. Here, the molar ratio indicated does not take into account the recirculation of aromatic hydroxy compound or dialkyl carbonate into the transesterification column via one or more overhead condenser(s) (cf. under (b)) or one or more bottom vaporizer(s) which may be present. (The ratio is based on the total amounts of dialkyl carbonate and aromatic hydroxy compound present in streams 21 and 22)

The stream (22) containing the dialkyl carbonate can, particularly in the case of processes carried out continuously, contain not only the dialkyl carbonate but also proportions of the aromatic hydroxy compound, the aliphatic hydroxy compound $R^1$—OH and/or $R^2$—OH formed in the reaction (reaction alcohol), very small amounts of the alkyl aryl carbonate and/or diaryl carbonate formed in the transesterification and undesirable secondary components formed in the reaction. The stream (22) containing the dialkyl carbonate can, for example, contain from 0 to 5% by weight, preferably from 0.05 to 3% by weight and particularly preferably from 0.05 to 2% by weight, of the reaction alcohol, from 0 to 40% by weight, preferably from 0 to 10% by weight, particularly preferably from 0 to 5% by weight, of the aromatic hydroxy compound, from 0 to 5% by weight of alkyl aryl carbonate, from 0 to 5% by weight of diaryl carbonate and from 0 to 5% by weight of other secondary compounds formed in the reaction (e.g. alkyl aryl ethers) or impurities which were originally present in the starting materials, in each case based on the total weight of the stream containing dialkyl carbonate.

The stream (22) containing the dialkyl carbonate preferably contains from 50 to 100% by weight of dialkyl carbonate, based on the total weight of the stream containing dialkyl carbonate, with the proportions of the individual abovementioned components adding up to 100% by weight. The stream (21) containing the aromatic hydroxy compound can, particularly in the case of processes carried out continuously, contain not only the aromatic hydroxy compound but also proportions of the dialkyl carbonate, the alkyl aryl carbonate and/or diaryl carbonate formed in the transesterification, very small amounts of the reaction alcohol and undesirable by-products formed in the reaction. For example, the content of the dialkyl carbonate can be from 0 to 50% by weight, the content of the reaction alcohol can be from 0 to 10% by weight, preferably from 0 to 5% by weight, the content of the alkyl aryl carbonate and the diaryl carbonate can in each case be from 0 to 10% by weight, preferably from 0 to 5% by weight, and the content of the undesirable by-products can be from 0 to 5% by weight, preferably from 0 to 1% by weight, in each case based on the total weight of the stream containing the aromatic hydroxy compound. In addition, the catalyst can be fed into the transesterification column with the stream (21) containing the aromatic hydroxy compound. In this case, the catalyst content is preferably from 0 to 5% by weight, based on the total weight of the stream containing the aromatic hydroxy compound. The stream (21) containing the aromatic hydroxy compound preferably contains from 50 to 100% by weight of aromatic hydroxy compound, based on the total weight of the stream containing the aromatic hydroxy compound, with the proportions of the individual above-mentioned components adding up to 100% by weight.

Transesterification catalysts known from the literature can be used for the reaction steps occurring in the dividing wall column. These are transesterification catalysts known from the literature for dialkyl carbonate-phenol transesterification, e.g. $AlX_3$, $TiX_3$, $UX_4$, $TiX_4$, $VOX_3$, $VX_5$, $ZnX_2$, $FeX_3$, $PbX_2$ and $SnX_4$, where X represents halogen, acetoxy, alkoxy or aryloxy radicals (DE-A 2 58 412). Particularly preferred catalysts which can be used according to the invention are metal compounds such as $AlX_3$, $TiX_4$, $PbX_2$ and $SnX_4$, for example titanium tetrachloride, titanium tetramethoxide, titanium tetraphenoxide, titanium tetraethoxide, titanium tetraisopropoxide, titanium tetradodecoxide, tin tetraisooctoxide and aluminium triisopropoxide. Very particularly preferred metal compounds are $TiX_4$. The metal compounds mentioned are preferably used in amounts of from 0.001 to 5% by weight, preferably from 0.005 to 5% by weight and particularly preferably from 0.01 to 5% by weight, based on the weight of the reaction mixture to be reacted.

For the purposes of the invention, halogen is fluorine, chlorine or bromine, preferably fluorine or chlorine, particularly preferably chlorine.

Further catalysts which can be used according to the invention are organotin compounds of the general formula $(R^{11})_{4-x}$—Sn$(Y)_x$, where Y is a radical $OCOR^{12}$, OH or OR, where $R^{12}$ is $C_1$-$C_{12}$-alkyl, $C_6$-$C_{12}$-aryl or $C_7$-$C_{13}$-alkylaryl, $R^{11}$ has, independently of $R^{12}$, one of the meanings of $R^{12}$ and x is an integer from 1 to 3, dialkyltin compounds having from 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctoxide, octyltin triisooctoxide, butylstannonic acid and octylstannonic acid in amounts of from 0.001 to 20% by weight (cf. EP 879, EP 880, EP 39 452, DE-A 34 45 555, JP 79/63023), polymeric tin compounds of the formula —[—RR$^{11}$Sn—O—]—, where R and R$^{11}$ each have, independently of one another, one of the meanings given above for $R^{12}$, for example poly[oxy(dibutylstannylene)]poly[oxy(dioctylstannylene)], poly[oxy(butylphenylstannylene)] and poly[oxy(diphenylstannylene)] (DE-A 34 45 552), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxanes) in amounts of from 0.001 to 20% by weight, preferably from 0.005 to 5% by weight, based on dialkyl carbonate (DE-A 40 06 520). Further tin compounds which can be used according to the invention are Sn(II) oxides of the general formula

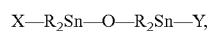

where X and Y are each, independently of one another, OH, SCN, $OR^{13}$, $OCOR^{13}$ or halogen and R is alkyl, aryl, where $R^{13}$ has the meaning given above for $R^{12}$ (EP 0 338 760).

Further catalysts which can be used according to the invention are lead compounds, optionally together with triorganophosphanes, a chelating compound or an alkalimetal halide, for example $Pb(OH)_2 \cdot 2PbCO_3$, $Pb(OCO-CH_3)_2$, $Pb(OCO-CH_3)_2 \cdot 2LiCl$, $Pb(OCO-CH_3)_2 \cdot 2PPh_3$ in amounts of from 0.001 to 1 mol, preferably from 0.005 to 0.25 mol per mole of dialkyl carbonate (JP 57/176932, JP 01/093580), and also other lead(II) and lead(IV) compounds such as PbO, $PbO_2$, red lead oxide, plumbites and plumbates (JP 01/093560), iron(III) acetate (JP 61/1 72 852), also copper salts and/or metal complexes, for example of alkali metals, zinc, titanium and iron (JP 89/005588).

It is also possible to use heterogeneous catalyst systems in the process of the invention. Examples are mixed oxides of silicon and titanium which can be obtained by cohydrolysis of silicon and titanium halides (JP 54/125617) or titanium dioxides having a high BET surface area of >20 $m^2/g$ (DE-A 40 36 594).

Preferred catalysts for the process of the invention are the abovementioned metal compounds $AlX_3$, $TiX_3$, $UX_4$, $TiX_4$, $VOX_3$, $VX_5$, $ZnX_2$, $FeX_3$, $PbX_2$ and $SnX_4$. Particular preference is given to $AlX_3$, $TiX_4$, $PbX_2$ and $SnX_4$, among which mention may be made by way of example of titanium tetrachloride, titanium tetramethoxide, titanium tetraphenoxide, titanium tetraethoxide, titanium tetraisopropoxide, titanium tetradodecoxide, tin tetraisooctoxide and aluminium triisopropoxide. Very particular preference is given to metal compounds $TiX_4$. Titanium tetramethoxide, titanium tetraphenoxide and titanium tetraethoxide are most preferred.

The catalyst is preferably introduced in dissolved or suspended form into the first reaction column together with the stream containing the aromatic hydroxy compound(s). As an alternative, the catalyst can also be fed in separately, for example in an alcohol corresponding to the reaction alcohol or a suitable inert solvent. If heterogeneous catalysts are used, these can be used in admixture with the packing elements mentioned, in suitable form instead of packing elements or as a bed on any installed column trays.

The liquid holdup provided in the reaction zone is such that the residence time of the liquid flowing through this reaction zone is in the range from 1 to 120 minutes, preferably from 10 to 60 minutes and particularly preferably from 15 to 40 minutes.

To set this residence time, it is possible to use ordered packings, random packing elements or trays or combinations of various internals (e.g. ordered packings and residence trays). Preference is given to using trays. Particular preference is given to using trays having a high liquid content. The latter is influenced by the level of the liquid. The level of the unsparged liquid on the trays is in the range from 20 to 400 mm, preferably from 40 to 300 mm and particularly preferably from 80 to 250 mm.

The number of theoretical plates in the reaction zone is, regardless of the type of internals selected, in the range from 5 to 100, preferably from 10 to 60 and particularly preferably from 20 to 40.

In the case of a heterogeneously catalyzed reaction, the reaction zone can contain the catalyst. In addition, intermediate vaporizers ($K_1ETRZ_{1-N}$) can be integrated to set the desired reaction temperature in a targeted manner.

The reaction is carried out in the range from 100 to 300° C., preferably 150-280° C. and particularly preferably from 180 to 245° C. The pressure in the reaction zone is preferably in the range from 0.5 to 20 bar, particularly preferably from 1 to 15 bar, very particularly preferably from 2 to 10 bar.

The vapour mixture containing dialkyl carbonate and alkyl alcohol formed during the reaction which is taken off at the top of the dividing wall column is preferably fed, after condensation at the top of the dividing wall column, in its entirety or in part to at least one further process step containing at least one distillation column for the separation of dialkyl carbonate and alkyl alcohol.

The separation of the dialkyl carbonate and the reaction alcohol is preferably carried out by distillation in one or more distillation columns or in a combination of distillation and membrane separation, hereinafter referred to as a hybrid process.

If reaction alcohol and dialkyl carbonate form an azeotrope (e.g. methanol and dimethyl carbonate), preference is given to using an at least two-stage process such as a two-pressure process, an extractive distillation, a heteroazeotropic distillation using a low-boiling entrainer or a hybrid process. Particular preference is given to employing the two-pressure process or a hybrid process. Very particular preference is given to employing the two-pressure process. Such processes are known in principle to those skilled in the art (cf., for example, Ullmann's Encyclopedia of Industrial Chemistry, Vol. 7, 2007, Chap. 6.4.. and 6.5.; Chemie Ingenieur Technik (67) 11/95).

If reaction alcohol and dialkyl carbonate do not form an azeotrope (e.g. ethanol and diethyl carbonate), the separation is preferably carried out in a single distillation column.

If reaction alcohol and dialkyl carbonate form an azeotrope, the distillate from a first distillation column of the process step for the separation of dialkyl carbonate and alkyl alcohol (reaction alcohol) preferably has a virtually azeotropic composition. In this case, this is preferably fed in a two-pressure process to at least one further distillation column which operates at an operating pressure which is below that of the first distillation column. As a result of the different operating pressure, the position of the azeotrope is shifted to smaller proportions of reaction alcohol. The bottom product obtained from this/these second or further distillation column(s) is reaction alcohol in a purity of from 90 to 100% by weight, based on the total weight of the isolated bottom product, and the distillate is a virtually azeotropic mixture. The second or further distillation column(s) which operate at a lower operating pressure is/are, in very particularly preferred embodiments, preferably operated using the heat of condensation of the overhead condenser(s) of the first distillation column.

In the two-pressure process, the pressure dependence of the azeotropic composition of a two-component mixture is utilized. In the case of a mixture of reaction alcohol (alkyl alcohol) and dialkyl carbonate, for example methanol and dimethyl carbonate, the azeotropic composition shifts to higher reaction alcohol contents with increasing pressure. If a mixture of these two components is fed to a column (dialkyl carbonate column) and the reaction alcohol content is below the azeotropic composition for the operating pressure of this column, a mixture of virtually azeotropic composition is obtained as distillate and virtually pure dialkyl carbonate is obtained as bottom product. The azeotropic mixture obtained in this way is fed to a further distillation column (alkyl alcohol column). This operates at an operating pressure lower than that of the dialkyl carbonate column. This results in the position of the azeotrope being shifted to lower reaction alcohol contents. This makes it possible to separate the azeotropic mixture obtained in the dialkyl carbonate column into a distillate having a virtually azeotropic composition and virtually pure reaction alcohol. The distillate from the alkyl alcohol column is returned to the dialkyl carbonate column at a suitable point.

The operating pressure of the alkyl alcohol column is preferably selected so that it can be operated using the waste heat from the dialkyl carbonate column. The operating pressure is in the range from 0.1 to 1 bar, preferably from 0.3 to 1 bar. The operating pressure of the dialkyl carbonate column is in the range from 1 to 50 bar, preferably from 2 to 20 bar.

A further preferred process for separating azeotropes of reaction alcohol and dialkyl carbonate is the hybrid process. In the hybrid process, a two-component mixture is separated by means of a combination of distillation and membrane processes. Here, use is made of the fact that the components can be at least partly separated from one another by means of membranes because of their polar properties and their different molecular weight. In the case of a mixture of reaction alcohol and dialkyl carbonate, for example methanol and dimethyl carbonate, pervaporation or vapour permeation using suitable membranes gives a mixture rich in reaction alcohol as permeate and a mixture depleted in reaction alcohol as retentate. If a mixture of these two components is fed to a column (dialkyl carbonate column) and the reaction alcohol content is below the azeotropic composition for the operating pressure of this column, a mixture having a reaction alcohol content which is significantly increased compared to the feed is obtained as distillate and virtually pure dialkyl carbonate is obtained as bottom product.

In the case of a hybrid process made up of distillation and vapour permeation, the distillate is taken off from the column in gaseous form. The gaseous mixture obtained in this way is fed, if appropriate after superheating, to a vapour permeation. In the operation of this, virtually the operating pressure of the column is set on the retentate side and a lower pressure is set on the permeate side. The operating pressure of the column is in the range from 1 to 50 bar, preferably from 1 to 20 bar and particularly preferably from 2 to 10 bar. The pressure on the permeate side is in the range from 0.05 to 2 bar. A fraction which is rich in reaction alcohol and has a reaction alcohol content of at least 70% by weight, preferably at least 90% by weight, based on the total weight of the fraction, is obtained on the permeate side. The retentate, which has a reduced reaction alcohol content compared to the distillate from the column, is condensed if appropriate and recirculated to the distillation column.

In the case of a hybrid process made up of distillation and pervaporation, the distillate is taken off from the column in liquid form. The mixture obtained in this way is, if appropriate after heating, fed to a pervaporation. In the operation of this, an operating pressure which is identical to or higher than that in the column is set on the retentate side and a lower pressure is set on the permeate side. The operation pressure of the column is in the range from 1 to 50 bar, preferably from 1 to 20 bar and particularly preferably from 2 to 10 bar. The pressure on the permeate side is in the range from 0.05 to 2 bar. A gaseous fraction which is rich in reaction alcohol and has a reaction alcohol content of at least 70% by weight, preferably at least 90% by weight, based on the total weight of the fraction, is obtained on the permeate side. The liquid retentate, which contains a proportion of reaction alcohol which is reduced compared to the distillate from the column, is recirculated to the distillation column. The vaporization of the permeate requires heat which may not be present in a sufficient quantity in the feed stream to the pervaporation. A membrane separation by means of pervaporation can therefore be heated by means of additional heat exchangers if appropriate, with these being integrated into or, if appropriate, installed between a plurality of pervaporation steps connected in series.

The separation of dialkyl carbonate and reaction alcohol in the case of a hybrid process is particularly preferably carried out by means of a combination of distillation and vapour permeation.

Regardless of the process selected for separating dialkyl carbonate and reaction alcohol, the process conditions such as pressure and temperature are advantageously selected so that the heat of condensation obtained from condensation in the condenser(s) of the further reaction column(s) and/or any intermediate condenser(s) present in the first reaction column can be utilized effectively.

The process of the invention is preferably carried out continuously.

On the feed side, there is at least one further section ($K_1TLO$) above the reaction zone. This does not contain any catalyst or in the case of a homogeneously catalyzed reaction may contain only very small amounts (<1% by weight), so that the transesterification does not take place or takes place to only a small extent in this section. The task of this section is the separation of the alkylaryl carbonate, higher-boiling compounds and preferably also the aromatic hydroxy compound from the dialkyl carbonate and reaction alcohol.

The number of theoretical plates in section $K_1TLO$ is, regardless of the type of internals selected, in the range from 1 to 100, preferably from 5 to 50 and particularly preferably from 10 to 30.

As internals, it is possible to use ordered packings, random packing elements or trays or combinations of various internals (e.g. structured packings and trays). Preference is given to using structured packings or random packing elements).

In a particular embodiment, this section ($K_1TLO$) also contains one or more intermediate condensers ($K_1ICTLO_{1-N}$). The use of intermediate condensers enables the heat of condensation to be removed at a higher temperature level and thus be used for heating other process sections or for generating a heating medium, for example heating steam.

Furthermore, at least one further section is located below the reaction zone ($K_1TLU$) on the feed side. The task of this section is the removal of the reaction alcohol and depletion of the dialkyl carbonate.

The number of theoretical plates in section $K_1TLU$ is, regardless of the type of internals selected, in the range from 1 to 100, preferably from 5 to 50 and particularly preferably from 10 to 30.

As internals, it is possible to use ordered packings, random packing elements or trays or combinations of various internals (e.g. ordered packings and trays). Preference is given to using trays.

When a homogeneous transesterification catalyst is used, the reaction also takes place in this section. In a particular embodiment of the process, intermediate vaporizers ($K_1ETLU_{1-N}$) are also present in this section.

On the offtake side, there are at least two sections. At least one section ($K_1TRO$) is present above the offtake point. This serves to deplete the reaction alcohol which is present in the liquid (11) fed in at the upper end of the section.

The number of theoretical plates in section $K_1TRO$ is, regardless of the type of internals selected, in the range from 1 to 100, preferably from 5 to 50 and particularly preferably from 10 to 30.

As internals, it is possible to use ordered packings, random packing elements or trays or combinations of various internals (e.g. ordered packings and trays). Preference is given to using trays.

In a particular embodiment, this section also contains one or more intermediate vaporizers ($K_1ETRO_{1-N}$).

Below the offtake point, there is at least one further section ($K_1TRU$). This serves to deplete components whose boiling point is above that of the dialkyl carbonate and which are present in the vapour stream (13) from the stripping section.

The number of theoretical plates in section $K_1TRO$ is, regardless of the type of internals selected, in the range from 1 to 100, preferably from 5 to 50 and particularly preferably from 10 to 30.

As internals, it is possible to use ordered packings, random packing elements or trays or combinations of various internals (e.g. ordered packings and trays). Preference is given to using trays.

In a particular embodiment, this section also contains one or more intermediate condensers ($K_1ICTRU_{1-N}$).

The side stream (5) can be taken off in gaseous or liquid form.

In the enrichment section ($K_1VT$) of the column, which consists of at least one section and, in particular embodiments, has one or more intermediate condensers ($K_1ICVT_{1-N}$), the reaction alcohol is concentrated.

The number of theoretical plates in the enrichment section is, regardless of the type of internals selected, in the range from 1 to 100, preferably from 5 to 50 and particularly preferably from 10 to 30.

As internals, it is possible to use ordered packings, random packing elements or trays or combinations of various internals (e.g. ordered packings and trays). Preference is given to using random packing elements or structured packings.

When diethyl carbonate (DEC) is used as one of the preferred dialkyl carbonates, the reaction alcohol can be taken off at the top of the column in virtually pure form. In the case of the particularly preferred dialkyl carbonate dimethyl carbonate (DMC), a methanol-dimethyl carbonate mixture having a virtually azeotropic composition is obtained at the top of the column.

The vapour (7) coming from the enrichment section ($K_1VT$) is partly or completely condensed. The condensate obtained is partly or entirely fed as runback (8) to the column. The distillate is thus partly taken off in gaseous form (3) and partly in liquid form (4). The way in which it is taken off depends on any subsequent further work-up of the distillation stream/streams. The proportion of gaseous distillate (3) in the total distillate stream, i.e. the total amount of the streams 3 and 4, can be in the range from 0 to 100%. The reflux ratio is given by the ratio of amount of runback to total distillate stream and is in the range from 0.5 to 50, preferably from 1 to 30 and particularly preferably from 5 to 20.

The liquid flowing down from the enrichment section is divided into two streams. One substream (10) is introduced into the upper section on the feed side ($K_1TLO$) and the remaining liquid (11) is fed to the upper end of the offtake side ($K_1TRO$). The proportion of the liquid fed to the feed side, based on the total amount of the liquid running down from the enrichment section ($K_1VT$), is from 5 to 95%, preferably from 10 to 80% and particularly preferably from 25 to 50%.

In the stripping section ($K_1AT$) of the RDWC, dialkyl carbonate and reaction alcohol are depleted. In a preferred embodiment of the process, the reactive dividing wall column is operated so that only small amounts of reaction alcohol are formed by transesterification in the stripping section of the column. Reaction alcohol formed in the stripping section and in the bottom of the column partly goes to the side stream offtake. The operation of the reactive dividing wall column should preferably be carried out so that the content of reaction alcohol in the side stream is less than 5% by weight, preferably less than 1% by weight and particularly preferably less than 0.5% by weight.

The number of theoretical plates in the stripping section is, regardless of the type of internals selected, in the range from 1 to 80, preferably from 5 to 40 and particularly preferably from 5 to 20.

As internals, it is possible to use ordered packings, random packing elements or trays or combinations of various internals (e.g. ordered packings and trays). Preference is given to using trays.

In a particular embodiment, one or more intermediate vaporizers ($K_1EAT_{1-N}$) are provided in the stripping section of the RDWC.

The vapour leaving the stripping section ($K_1AT$) is divided into a vapour stream to the feed side (12) and a vapour stream to the offtake side (13). The proportion of the vapour stream to the feed side (12) based on the total vapour stream, i.e. the sum of streams 12 and 13, is from 5 to 95%, preferably from 10 to 80% and particularly preferably from 30 to 75%.

The liquid (9) running down from the stripping section ($K_1AT$) is concentrated further in one or more vaporizers. In a particular embodiment, the vaporizer(s) $K_1E_{1-N}$ serve(s) as sole heat supply for the reaction K1.

The temperature at the bottom is in the range from 100 to 300° C., preferably from 150 to 280° C. and particularly preferably from 200 to 250° C.

The bottom product from the reaction K1 (6) contains aromatic hydroxy compound, alkyl aryl carbonate, diaryl carbonate, dialkyl carbonate, catalyst and secondary compounds (definition of secondary compounds: compounds which are present as impurities in the starting materials or are formed as undesirable by-products in the reaction) and is, in a preferred embodiment, fed to at least one further reaction stage in which the alkyl aryl carbonate preferably reacts further by disproportionation to form the diaryl carbonate.

If the dialkyl carbonate is the particularly preferred dimethyl carbonate, a mixture of methanol and dimethyl carbonate having a virtually azeotropic composition is obtained as distillate (stream 3 and/or 4). To make a higher concentration of the reaction alcohol possible, at least one further work-up step is required. One possible way of concentrating the reaction alcohol further is a membrane process. Preferred membrane processes are pervaporation and vapour permeation.

Figure 2:
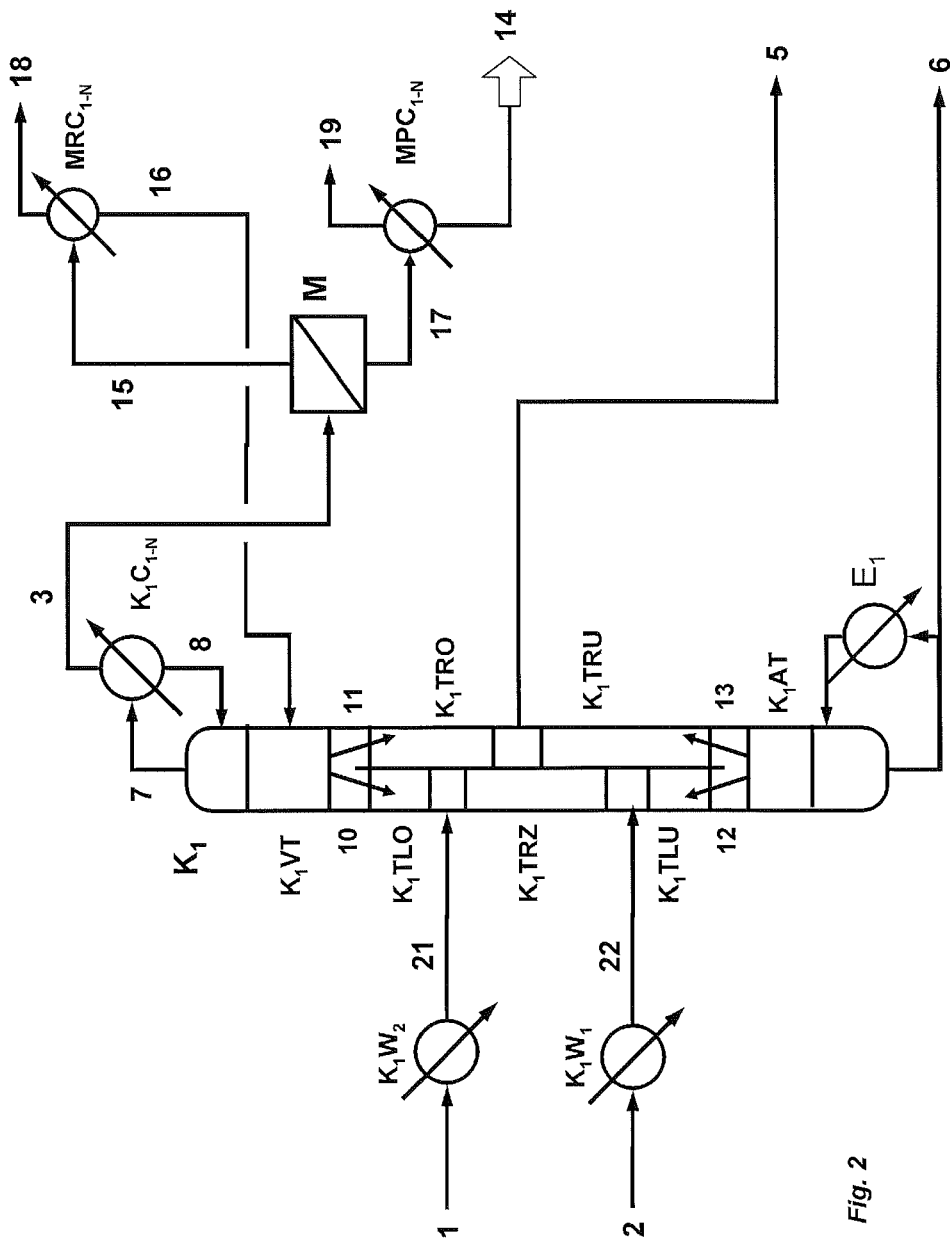
FIG. 2 depicts a particular embodiment of the reactive dividing wall column with separation of the gaseous distillate in a membrane separation.

Such a process variant using vapour permeation is described by way of example in FIG. 2.

In this preferred embodiment, the distillate (3) is taken off exclusively in gaseous form and fed to a membrane separation (M) by means of pervaporation. A methanol-rich fraction containing more than 70% by weight, preferably more than 90% by weight, of methanol is obtained as permeate (17). A low-methanol fraction containing less than 60% by weight, preferably less than 50% by weight, of methanol is obtained as retentate (15). The methanol-rich permeate (17) is condensed (condenser $MPC_{1-N}$) and discharged from the process. The retentate (15) is, in a preferred embodiment, condensed (condenser $MRC_{1-N}$) and recirculated to the reactive dividing wall column in the region of the enrichment section ($K_1VT$).

Figure 3:
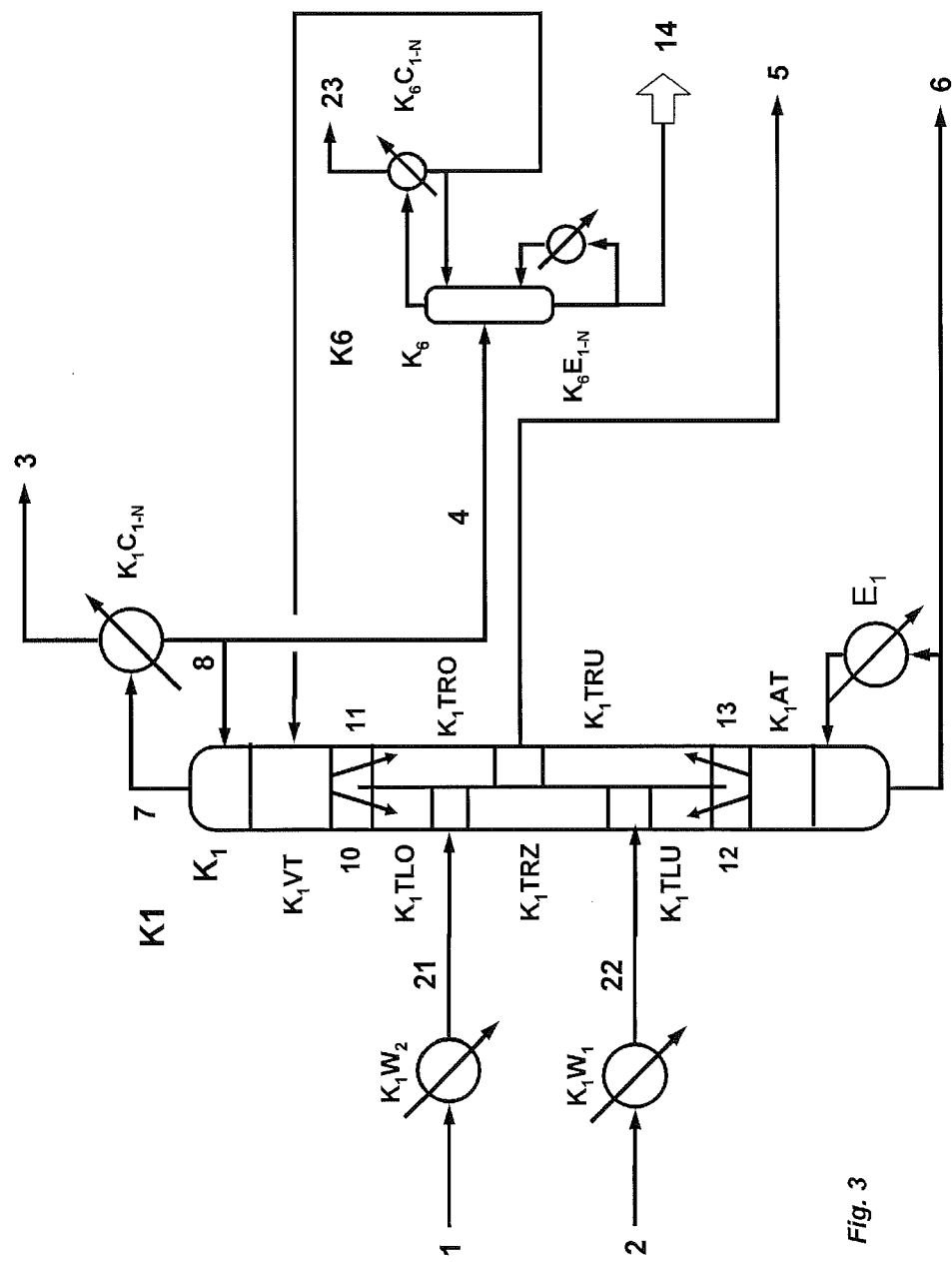
FIG. 3 depicts a particular embodiment of the reactive dividing wall column with separation of the liquid distillate in a distillation column.

A further preferred embodiment for further concentrating the methanol is depicted in FIG. 3. In this case, the distillate is preferably taken off in liquid form (4). The gaseous distillate stream (3) contains inerts (e.g. nitrogen or carbon dioxide) and also secondary compounds having boiling points below that of methanol or of the methanol/dimethyl carbonate azeotrope.

The liquid distillate (4) having a virtually azeotropic composition is fed to a further distillation column ($K_6$) which is operated at a pressure below that of the reactive dividing wall column. Preference is given to setting a pressure of less than 2 bar, preferably less than 1 bar. Owing to the lower operating pressure, the position of the azeotropic point shifts to lower methanol contents. A distillate fraction having a virtually azeotropic composition and a bottom fraction containing pure methanol are obtained. The distillate fraction is recirculated to the reactive dividing wall column at a suitable point, preferably in the enrichment section ($K_1VT$).

Figure 4:
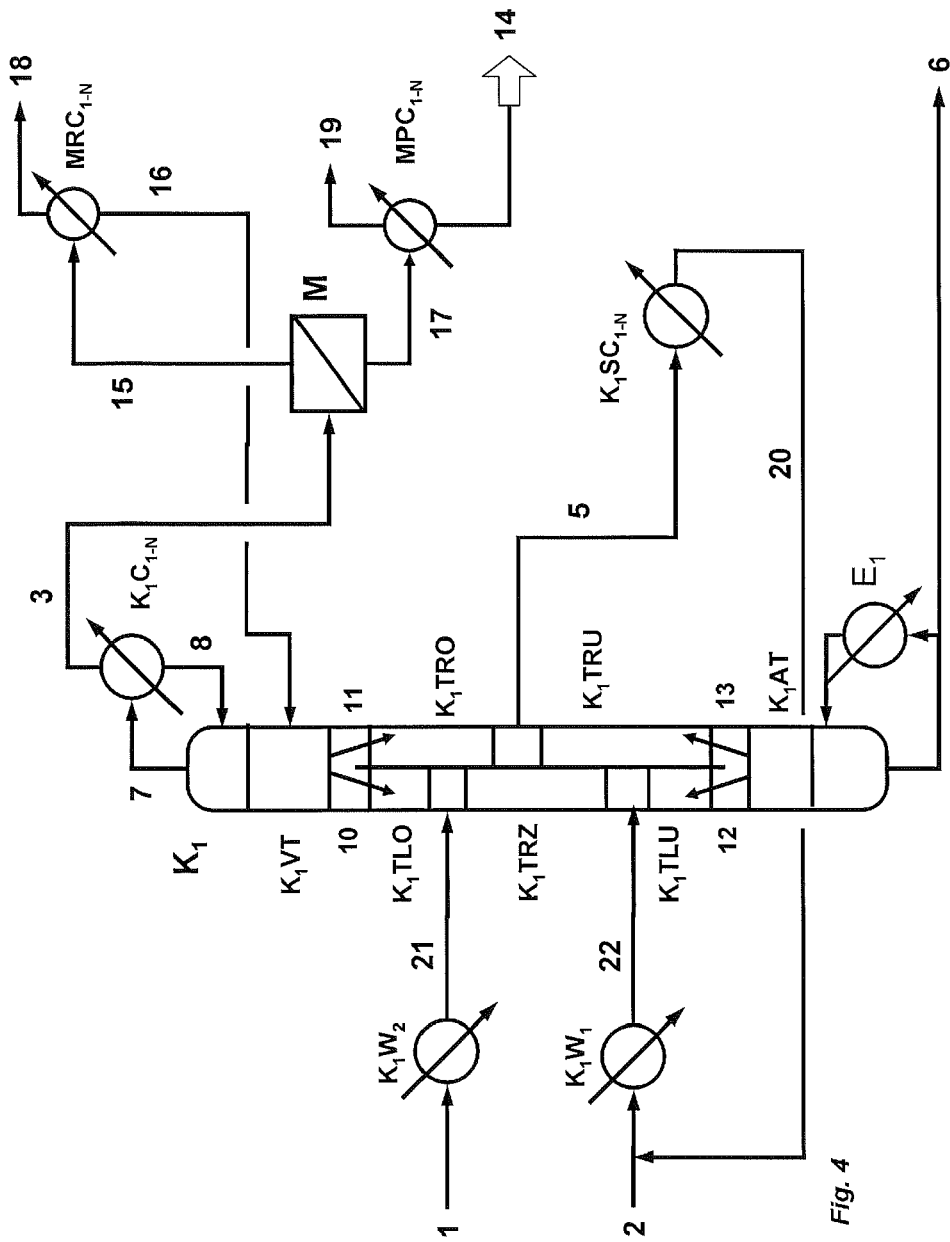
FIG. 4 depicts a particular embodiment of the reactive dividing wall column with separation of the gaseous distillate in a membrane separation, condensation of the gaseous side stream and mixing of the resulting condensate with a feed stream.

FIG. 4 describes a particular embodiment of the reactive dividing wall column ($K_1$) with separation of the gaseous distillate in a membrane separation. In contrast to the embodiment shown in FIG. 2, the side stream (5) containing dimethyl carbonate is taken off in gaseous form. This is condensed, if appropriate mixed with a further stream (2) containing dimethyl carbonate and subsequently, if appropriate after vaporization (vaporizer $K_1W_1$), recirculated to the reaction zone on the feed side of the reactive dividing wall column.

Figure 5:
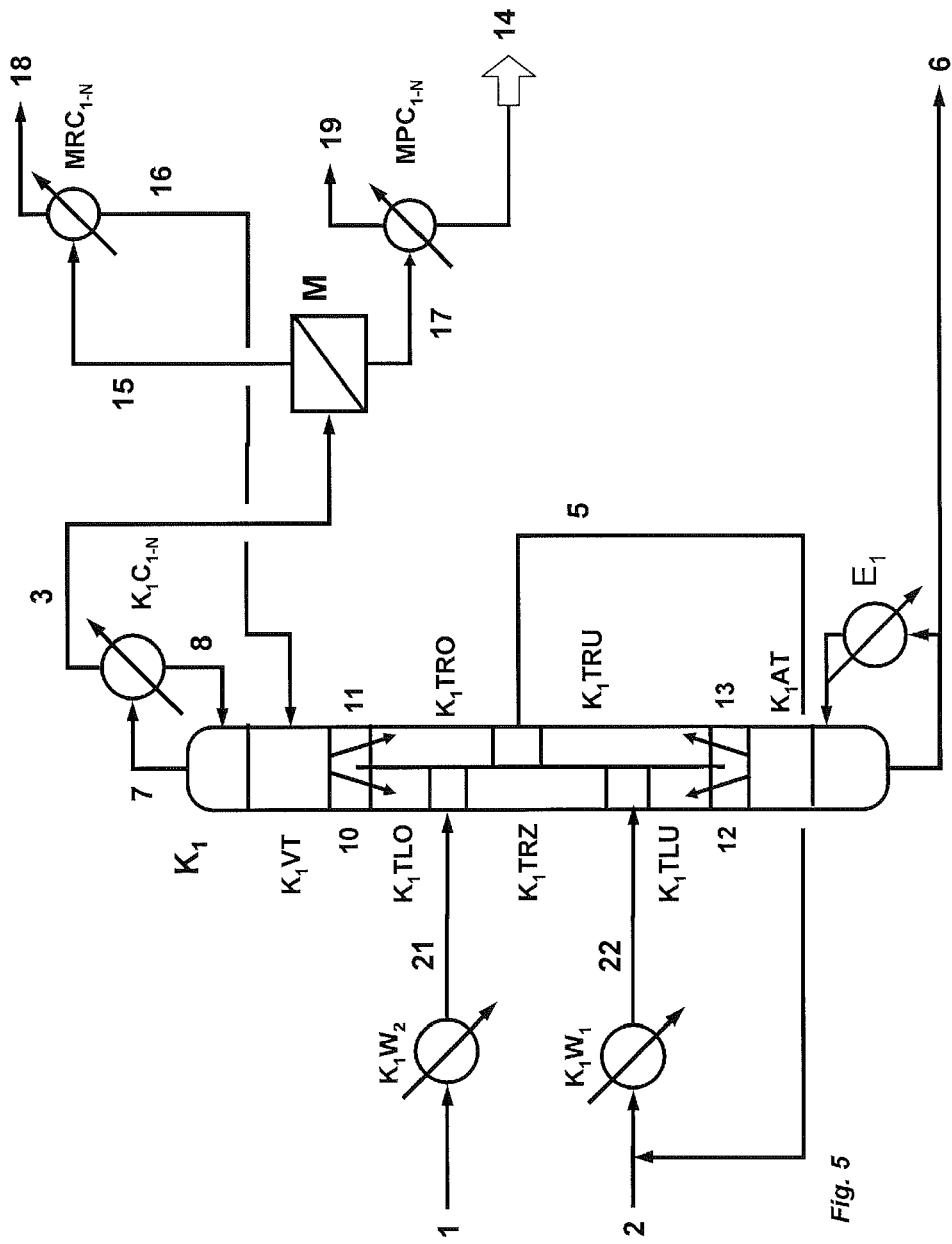
FIG. 5 depicts a particular embodiment of the reactive dividing wall column with separation of the gaseous distillate in a membrane separation, offtake of a liquid side stream from the reactive dividing wall column and mixing of this side stream with a feed stream.

FIG. 5 describes a particular embodiment of the reactive dividing wall column with separation of the gaseous distillate in a membrane separation, in which the side stream (5) containing dimethyl carbonate is taken off as liquid from the reactive dividing wall column. The liquid side stream is, if appropriate, mixed with a further stream (2) containing dimethyl carbonate and subsequently, if appropriate after vaporization, recirculated to the reaction zone on the feed side of the reactive dividing wall column.

Figure 6:
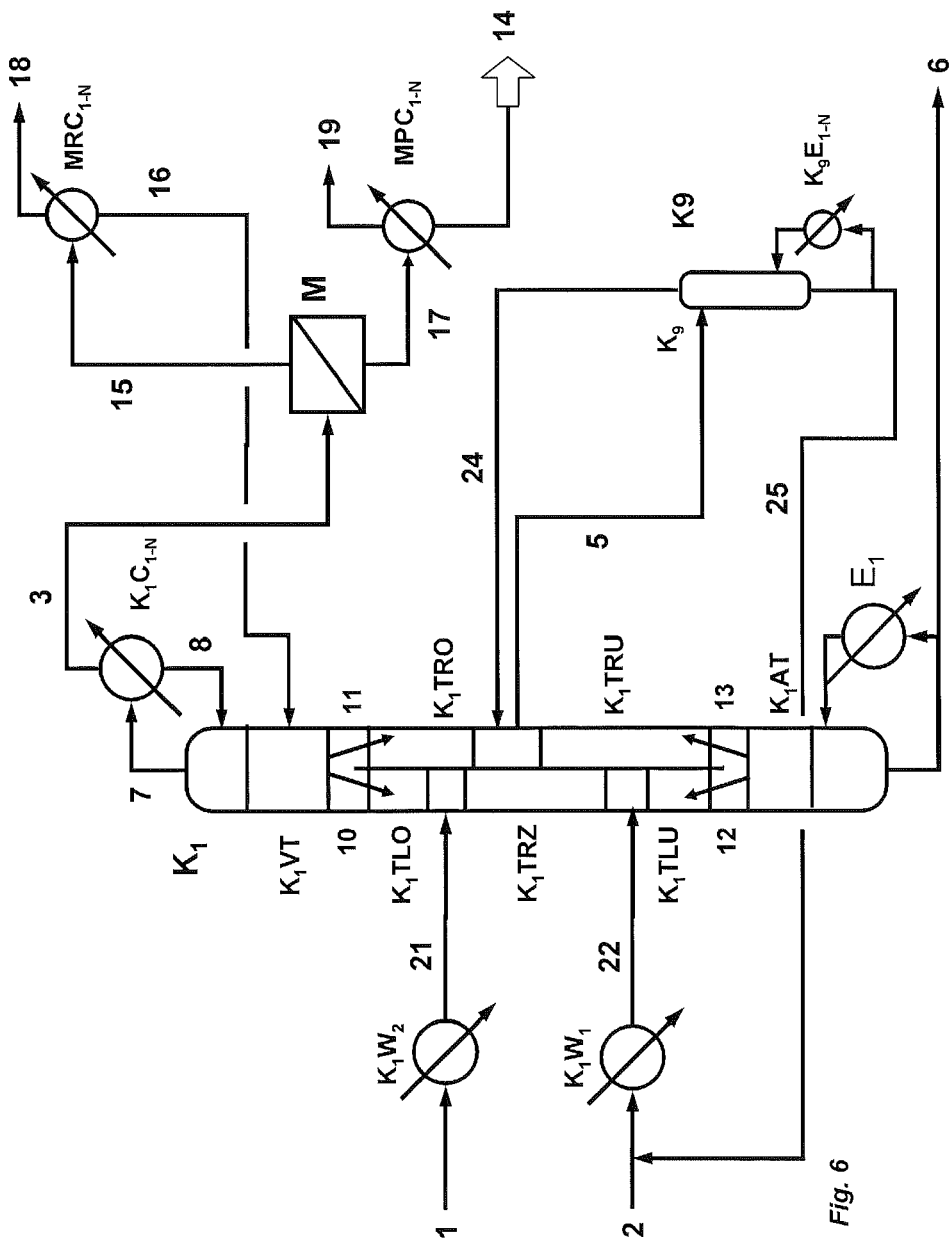
FIG. 6 depicts a particular embodiment of the reactive dividing wall column with separation of the gaseous distillate in a membrane separation, offtake of a liquid side stream from the reactive dividing wall column, removal of any reaction alcohol still present in a distillation column and mixing of the bottom product of this distillation column with a feed stream.

FIG. 6 describes a particular embodiment of the reactive dividing wall column with separation of the gaseous distillate in a membrane separation.

In this case, the side stream is taken off in liquid form and fed to a further distillation column to separate off any reaction alcohol still present.

When the reaction is carried out appropriately, in particular when using a homogeneous catalyst, the transesterification also takes place in the stripping section ($K_1AT$) of the reactive dividing wall column. As a result, reaction alcohol also goes into the offtake side of the reactive dividing wall column and thus sometimes also into the liquid side stream. If the residual content of reaction alcohol has to meet demanding requirements, this has to be separated off in a further step.

This can be carried out, as depicted in FIG. 6, by feeding the liquid side stream to a side stream stripper ($K_9$). A vapour fraction (24) is obtained at the top of this stripping column and is recirculated to the reactive dividing wall column at a suitable point, preferably above the liquid side stream offtake (5). The bottom product (25) from the stripping column ($K_9$) is, if appropriate, mixed with a further stream (2) containing dimethyl carbonate and subsequently, if appropriate after vaporization, recirculated to the reaction zone ($K_1RZ$) on the feed side of the reactive dividing wall column.

Figure 7:
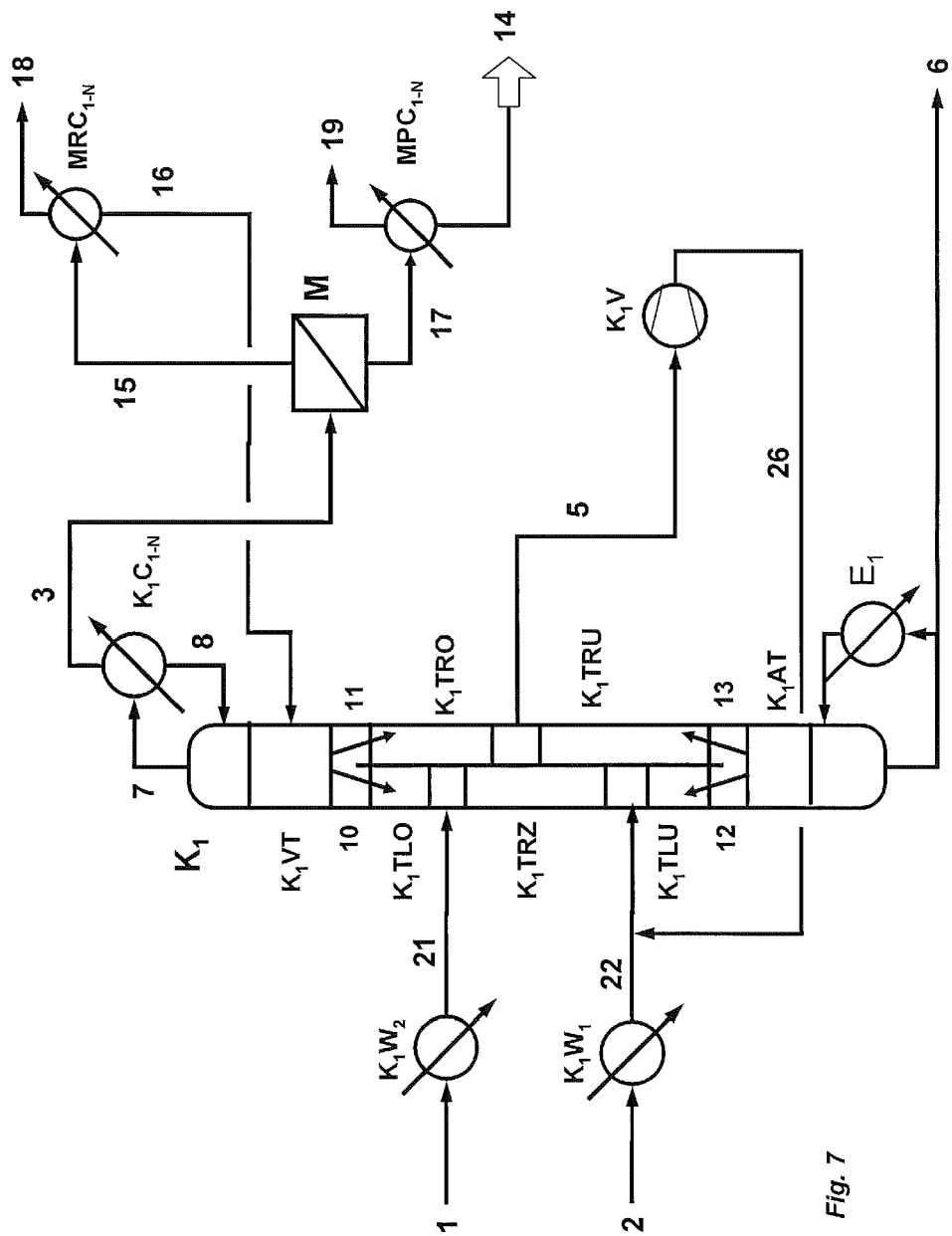
FIG. 7 depicts a particular embodiment of the reactive dividing wall column with separation of the gaseous distillate in a membrane separation, compression of the gaseous side stream and mixing of the resulting superheated vapour with a heated and optionally partly vaporized feed stream.

FIG. 7 describes a particular embodiment of the reactive dividing wall column with separation of the gaseous distillate in a membrane separation. In this case, the side stream is taken off in vapour form.

This side stream is subsequently brought to a higher pressure by means of an apparatus for increasing the pressure ($K_1V$), preferably by means of a compressor or blower, and, if appropriate after superheating and mixing with a further gaseous stream containing dimethyl carbonate, recirculated to the reaction zone ($K_1RZ$) on the feed side of the reactive dividing wall column.

FIG. 1 describes a first transesterification step by means of a reactive dividing wall column ("in general")

FIG. 2 describes a particular embodiment of the reactive dividing wall column with separation of the gaseous distillate in a membrane separation FIG. 3 describes a particular embodiment of the reactive dividing wall column with separation of the liquid distillate in a distillation column.

FIG. 4 describes a particular embodiment of the reactive dividing wall column with separation of the gaseous distillate in a membrane separation, condensation of the gaseous side stream and mixing of the resulting condensate with a feed stream.

FIG. 5 describes a particular embodiment of the reactive dividing wall column with separation of the gaseous distillate in a membrane separation, offtake of a liquid side stream from the reactive dividing wall column and mixing of this side stream with a feed stream.

FIG. 6 describes a particular embodiment of the reactive dividing wall column with separation of the gaseous distillate in a membrane separation, offtake of a liquid side stream from the reactive dividing wall column, removal of any reaction alcohol still present in a distillation column and mixing of the bottom product of this distillation column with a feed stream.

FIG. 7 describes a particular embodiment of the reactive dividing wall column with separation of the gaseous distillate in a membrane separation, compression of the gaseous side stream and mixing of the resulting superheated vapour with a heated and optionally partly vaporized feed stream.

Figure 8:
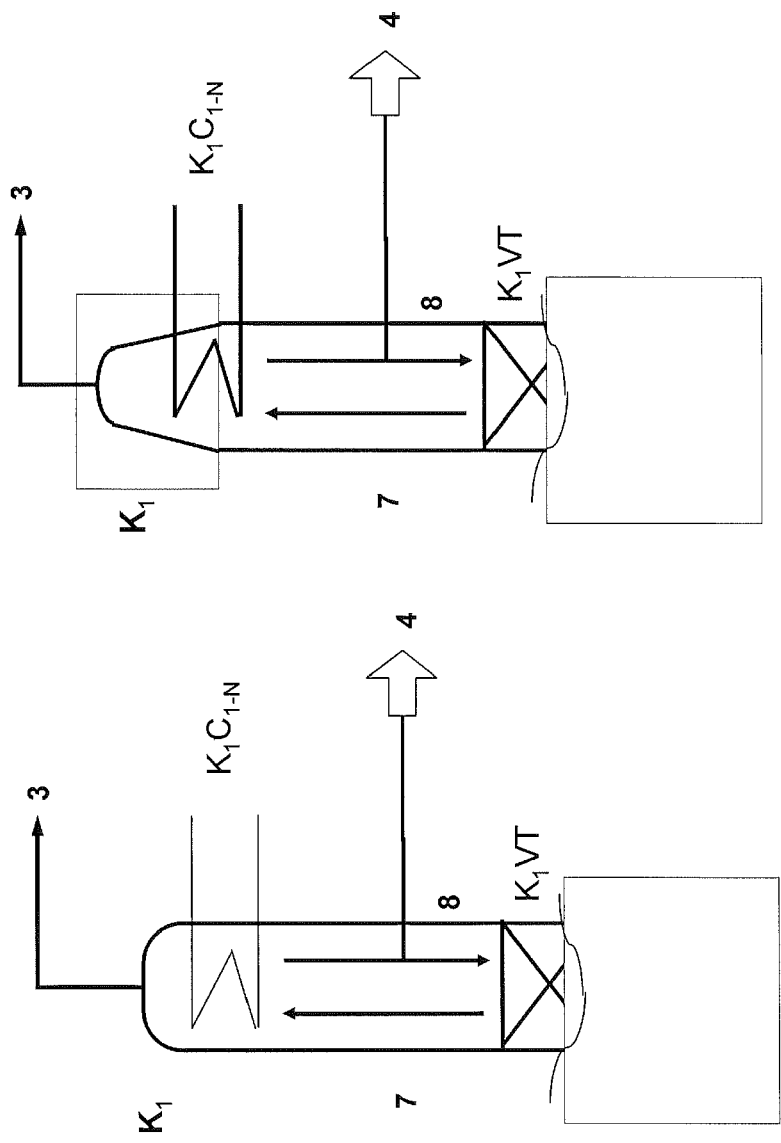
FIG. 8 depicts the process stage with condensation in an integrated condenser.

FIG. 8 describes the process stage with condensation in an integrated condenser.

Figure 9:
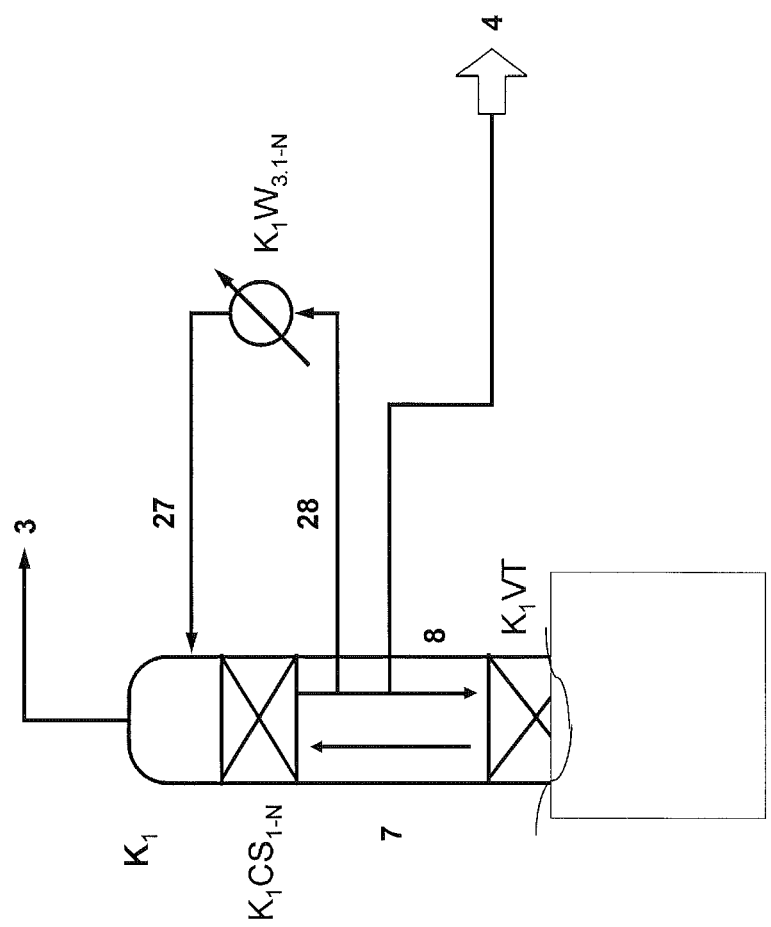
FIG. 9 depicts the process stage with condensation in a bed of packing.

FIG. 9 describes the process stage with condensation in a bed of packing.

The figures serve to illustrate the invention by way of example and are not to be construed as a restriction.

In FIGS. 1 to 9, the symbols have the following meanings:
$K_1$ Process section of reaction
$K_1$: Reactive dividing wall column
$K_1C_{1-N}$ Condenser(s) 1-N
$K_1E_{1-N}$ Vaporizers 1 to N
$K_1IC_{1-N}$ Intermediate condenser(s) 1 to N
T Dividing wall
$K_1VT_{1-N}$ Enrichment section (optionally a plurality of/1-N sections)
$K_1W_{1,1-N}$ Preheater/vaporizer/superheater for stream containing dialkyl carbonate
$K_1W_{2,1-N}$ Preheater/vaporizer for feed stream containing aromatic hydroxy compound
$K_1TRZ$ Reaction zone (feed side of the dividing wall)
$K_1E\_TRZ_{1-N}$ Intermediate vaporizers 1 to N in the region of the reaction zone
$K_1TLO$ Section above the reaction zone on the feed side
$K_1ICTLO_{1-N}$ Intermediate condenser(s) 1-N in $K_1TLO$
$K_1TLU$ Section below the reaction zone on the feed side
$K_1ETLU_{1-N}$ Intermediate vaporizers 1-N in $K_1TLU$
$K_1TRO$ Section above the offtake on the offtake side
$K_1ETLO_{1-N}$ Intermediate vaporizers 1-N in $K_1TRO$
$K_1TRU$ Section below the offtake on the offtake side
$K_1ICTRU_{1-N}$ Intermediate condenser(s) 1-N in $K_1TRU$
$K_1AT$ Stripping section
$K_1E\_AT_{1-N}$ Intermediate vaporizers 1-N in the stripping section
$K_1SC_{1-N}$ Side stream condenser(s)
$K_1V$ Side stream compressor
$K_6$ Process section for distillation of the reaction alcohol (RAK)
$K_6$ Reaction alcohol distillation column (RAKD)
$K_6C_{1-N}$ Condenser(s) 1 to N
$K_6E_{1-N}$ Vaporizers 1 to N
$K_6VT$ Enrichment section of the RAKD
$K_6AT$ Stripping section of the RAKD
  Particular embodiment: Hybrid process comprising K1 and membrane separation
M Membrane separation (vapour permeation or pervaporation)
MRC Condenser for retentate after the membrane separation
MPC Condenser for permeate after the membrane separation
K9: Process section for removal of reaction alcohol from dialkyl carbonate by distillation
$K_9$: Distillation column
$K_9C_{1-N}$: Condenser (optionally multistage)
$K_9E_{1-N}$: Vaporizer for bottom product (optionally multistage)
$K_9VT$: Enrichment section
$K_9AT$: Stripping section
  Particular embodiment: Condensation for the example of process section K1
$K_1CS_{1-N}$: Column segment with direct condensation
$K_NW_{3,1-N}$: Heat exchanger for cooling a circulation stream for the condensation in $K_NCS_{1-N}$
Furthermore, the following streams are shown in FIGS. 1 to 9:
1 Feed stream containing aromatic hydroxy compound
2 Feed stream containing dialkyl carbonate
3 Gaseous distillate from reaction K1
4 Liquid distillate from reaction K1
5 Gaseous or liquid side stream from $K_1$
6 Bottom product from reaction K1
7 Gaseous stream at the top of $K_1$ to condenser(s) $K_1C_{1-N}$
8 Runback of $K_1$
9 Liquid outflow from stripping section of $K_1$
10 Liquid outflow from enrichment section of $K_1$ to feed side of the dividing wall
11 Liquid outflow from enrichment section of $K_1$ to offtake side of the dividing wall
12 Vapour stream from the stripping section of $K_1$ to feed side of the dividing wall
13 Vapour stream from the stripping section of $K_1$ to offtake side of the dividing wall
14 Reaction alcohol which has been concentrated
15 Retentate from the membrane separation (M) to the condenser ($MRC_{1-N}$)
16 Liquid retentate to reaction (K1)
17 Permeate from the membrane separation (M) to the condenser ($MPC_{1-N}$)
18 Residual vapour stream after condenser ($MRC_{1-N}$)
19 Residual vapour stream after condenser ($MPC_{1-N}$)
20 Liquid stream containing dialkyl carbonate to reaction K1
21 Stream containing aromatic hydroxy compound to $K_1$
22 Stream containing dialkyl carbonate to $K_1$
23 Residual vapour stream after $K_6C_{1-N}$
24 Vapour stream at the top of $K_9$
25 Bottom product from process section K9

26 Superheated vapour stream containing dialkyl carbonate after compressor $K_1V$ to $K_1$ 27 External circuit for condensation in a column segment before cooling 28 External circuit for condensation in a column segment after cooling All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1

396.9 kg/h of a mixture (21) comprising 85.91% by weight of phenol, 9.32% by weight of dimethyl carbonate, 3.22% by weight of diphenyl carbonate, 1.55% by weight of titanium tetraphenoxide are fed to a reactive dividing wall column ($K_1$) comprising an enrichment section ($K_1VT$) having 19 theoretical plates, a stripping section ($K_1AT$) having 9 theoretical plates, a dividing wall which divides the column between enrichment section and stripping section into a feed side and an offtake side, an upper section on the feed side ($K_1LO$) having 10 theoretical plates, a reaction zone ($K_1TRZ$) on the feed side of the dividing wall having 30 reaction trays (holdup/tray: 12 l), a further section on the feed side ($K_1LU$) below the reaction zone having 10 theoretical plates, an upper section on the offtake side ($K_1RO$) above the side stream offtake (5) having 15 theoretical plates, a lower section on the offtake side ($K_1RU$) below the side stream offtake (5) having 15 theoretical plates and a stripping section $K_1AT$ having 6 trays (holdup: 12 l) at the upper end of the reaction zone ($K_1TRZ$). 539 kg/h of a vapour mixture (22) comprising 98.9% by weight of dimethyl carbonate, 0.9% by weight of phenol, 0.2% by weight of anisole are fed in at the lower end of the reaction zone ($K_1RZ$).

The reactive dividing wall column is operated at a pressure at the top of 3.6 bar (absolute) and a reflux ratio of 18.

32% of the liquid (10) running down from the enrichment section are fed to the upper section of the feed side ($K_1TLO$), corresponding to an amount of 317 kg/h. The remaining liquid (11) is fed to the upper end of the offtake side ($K_1TRO$).

A temperature of 230° C. is set in the bottom of the column, with a kettle-type vaporizer being used as bottom vaporizer ($K_1E_1$). Heating steam (40 bara) is used as heating medium.

The vapour leaving the stripping section is distributed uniformly over feed side and offtake side.

The distillate (3) is taken off exclusively in gaseous form. 50 kg/h of a gaseous distillate stream comprising 68% by weight of methanol and 31.9% by weight of dimethyl carbonate are obtained. The azeotropic composition at the operating pressure indicated is 76% by weight.

In the side stream (5), 515 kg/h comprising 91.3% by weight of dimethyl carbonate, 8.5% by weight of phenol and 0.2% by weight of methanol are taken off as liquid.

In addition, 394 kg/h of a product mixture (6) comprising 62.2% by weight of phenol, 20.6% by weight of methyl phenyl carbonate, 5.3% by weight of diphenyl carbonate, 10% by weight of dimethyl carbonate, 0.3% by weight of anisole and 1.6% by weight of titanium tetraphenoxide are obtained as bottom product from the reaction K1.

Example 2

The same reactive dividing wall column as described in Example 1 is used. 396.9 kg/h of a mixture (21) comprising 85.91% by weight of phenol, 9.32% by weight of dimethyl carbonate, 3.22% by weight of diphenyl carbonate, 1.55% by weight of titanium tetraphenoxide are fed in at the upper end of the reaction zone ($K_1TRZ$).

312.9 kg/h of a vapour mixture (22) which comprises 86.1% by weight of dimethyl carbonate, 13.7% by weight of phenol and 0.2% by weight of methanol and has been superheated by 10° C. are fed in at the lower end of the reaction zone ($K_1RZ$).

The reactive dividing wall column is operated at a pressure at the top of 3.6 bar (absolute) and a reflux ratio of 14.2.

37% (202 kg/h) of the liquid (10) running down from the enrichment section are fed to the upper section of the feed side ($K_1TLO$). The remaining liquid (11) is fed in at the upper end of the offtake side ($K_1TRO$).

A temperature of 230° C. is set in the bottom of the column, with a kettle-type vaporizer being used as bottom vaporizer ($K_1E_1$). Heating steam (40 bara) is used as heating medium.

The vapour leaving the stripping section is distributed uniformly over feed side and offtake side.

The distillate (3) is taken off exclusively in gaseous form. 20.5 kg/h of a gaseous distillate stream comprising 68% by weight of methanol and 31.9% by weight of dimethyl carbonate is obtained. The azeotropic composition at the operating pressure indicated is 76% by weight.

In the side stream (5), 263 kg/h comprising 83.4% by weight of dimethyl carbonate, 16.3% by weight of phenol and 0.3% by weight of methanol are taken off as liquid.

The side stream is mixed with a further dimethyl carbonate stream (2) having a flow rate of 50 kg/h and a dimethyl carbonate content of 100%, vaporized, superheated and recirculated to the reactive dividing wall column below the reaction zone ($K_1RZ$).

Furthermore, 426.4 kg/h of a product mixture (6) comprising 70.1% by weight of phenol, 15.3% by weight of methyl phenyl carbonate, 3.4% by weight of diphenyl carbonate, 9.6% by weight of dimethyl carbonate, 0.02% by weight of anisole and 1.44% by weight of titanium tetraphenoxide are obtained as bottom product from the reaction column K1.

Example 3

The same reactive dividing wall column as described in Examples 1 and 2 is used. 396.9 kg/h of a mixture (21) comprising 85.91% by weight of phenol, 9.32% by weight of dimethyl carbonate, 3.22% by weight of diphenyl carbonate, 1.55% by weight of titanium tetraphenoxide are fed in at the upper end of the reaction zone ($K_1TRZ$).

386.2 kg/h of a vapour mixture (22) which comprises 89.6% by weight of dimethyl carbonate, 10.2% by weight of phenol and 0.2% by weight of methanol and has been superheated by 10° C. are fed in at the lower end of the reaction zone ($K_1RZ$).

The reactive dividing wall column is operated at a pressure at the top of 3.6 bar (absolute) and a reflux ratio of 10.4.

37% (258.2 kg/h) of the liquid (10) running down from the enrichment section are fed to the upper section of the feed side ($K_1TLO$). The remaining liquid (11) is fed in at the upper end of the offtake side ($K_1TRO$).

A temperature of 230° C. is set in the bottom of the column, with a kettle-type vaporizer being used as bottom vaporizer ($K_1E_1$). Heating steam (40 bara) is used as heating medium.

The vapour leaving the stripping section is uniformly distributed over feed side and offtake side.

The distillate (3) is taken off exclusively in gaseous form. 33 kg/h of a gaseous distillate stream comprising 68% by weight of methanol and 31.7% by weight of dimethyl carbonate are obtained. The azeotropic composition at the operating pressure indicated is 76% by weight.

In the side stream (5), 336.2 kg/h comprising 88.1% by weight of dimethyl carbonate, 11.7% by weight of phenol and 0.2% by weight of methanol are taken off as liquid.

The side stream is mixed with a further dimethyl carbonate stream (2) having a flow rate of 50 kg/h and a dimethyl carbonate content of 100%, vaporized, superheated and recirculated to the reactive dividing wall column below the reaction zone ($K_1RZ$).

336.2 kg/h of a mixture (6) comprising 68.15% by weight of phenol, 16.71% by weight of methyl phenyl carbonate, 3.9% by weight of diphenyl carbonate, 9.8% by weight of dimethyl carbonate, 0.01% by weight of anisole and 1.43% by weight of titanium tetraphenoxide are obtained as bottom product from the reaction column K1.

The gaseous distillate is fed to a membrane separation (M) by means of pervaporation. 16.2 kg/h of a gaseous stream comprising 40% by weight of methanol are obtained as retentate and are, after condensation, fed into the upper third of the enrichment section ($K_1VT$) of the reactive dividing wall column.

A methanol-rich fraction (17) comprising 95% by weight of methanol is obtained as permeate.

Example 4

The same combination of reactive dividing wall column and pervaporation as described in Example 3 is used.

In addition, the liquid side stream (5) from the reactive dividing wall column ($K_1$) is fed to a side stream stripper ($K_9$) having only one stripping section containing 14 theoretical plates. The side stream stripper does not have a condenser and operates at an operating pressure of 4 bar, which is about 10 mbar above the pressure in the RDWC in the region of the side stream offtake. The side stream stripper ($K_9$) is heated by means of a circulation vaporizer using heating steam (6 bar).

396.9 kg/h of a mixture (21) comprising 85.91% by weight of phenol, 9.32% by weight of dimethyl carbonate, 3.22% by weight of diphenyl carbonate, 1.55% by weight of titanium tetraphenoxide, are fed in at the upper end of the reaction zone ($K_1TRZ$).

381.9 kg/h of a vapour mixture (22) which comprises 89.7% by weight of dimethyl carbonate, 10.1% by weight of phenol and 0.2% by weight of methanol and has been superheated by 10° C. are fed at the lower end of the reaction zone ($K_1RZ$).

The reactive dividing wall column is operated at a pressure at the top of 3.6 bar (absolute) and a reflux ratio of 10.4.

37% (258.8 kg/h) of the liquid (10) running down from the enrichment section are fed to the upper section of the feed side ($K_1TLO$). The remaining liquid (11) is fed in at the upper end of the offtake side ($K_1TRO$).

A temperature of 230° C. is set in the bottom of the column, with a kettle-type vaporizer being used as bottom vaporizer ($K_1E_1$). Heating steam (40 bara) is used as heating medium.

The vapour leaving the stripping section is uniformly distributed over feed side and offtake side.

The distillate (3) is taken off exclusively in gaseous form. 33 kg/h of a gaseous distillate stream comprising 68% by weight of methanol and 31.7% by weight of dimethyl carbonate are obtained. The azeotropic composition at the operating pressure indicated is 76% by weight.

In the side stream (5), 336.9 kg/h comprising 88.3% by weight of dimethyl carbonate, 11.44% by weight of phenol and 0.23% by weight of methanol are taken off as liquid.

The bottom product from the side stream stripper (K9) has a methanol content of less than 0.2 by weight and is mixed with a further dimethyl carbonate stream (2) having a flow rate of 50 kg/h and a dimethyl carbonate content of 100%, vaporized, superheated and recirculated to the reactive dividing wall column below the reaction zone ($K_1RZ$).

5 kg/h are taken off in gaseous form as overhead product and recirculated to the reactive dividing wall column above the side stream offtake (5).

430.1 kg/h of a mixture (6) comprising 68.15% by weight of phenol, 16.71% by weight of methyl phenyl carbonate, 3.9% by weight of diphenyl carbonate, 9.8% by weight of dimethyl carbonate, 0.01% by weight of anisole and 1.43% by weight of titanium tetraphenoxide are obtained as bottom product from the reaction column K1.

The gaseous distillate is fed to a membrane separation (M) by means of pervaporation. 16.2 kg/h of a gaseous stream comprising 40% by weight of methanol are obtained as retentate and are, after condensation, fed into the upper third of the enrichment section ($K_1VT$) of the reactive dividing wall column.

A methanol-rich fraction (17) comprising 95% by weight of methanol is obtained as permeate.

Example 5

The same combination of reactive dividing wall column, pervaporation and side stream stripping as described in Example 4 is used.

However, the reactive dividing wall column is operated at an increased reflux ratio of 13.4.

396.9 kg/h of a mixture (21) comprising 85.91% by weight of phenol, 9.32% by weight of dimethyl carbonate, 3.22% by weight of diphenyl carbonate, 1.55% by weight of titanium tetraphenoxide are fed in at the upper end of the reaction zone ($K_1TRZ$).

514.8 kg/h of a vapour mixture (22) which comprises 94.4% by weight of dimethyl carbonate, 5.4% by weight of phenol and 0.2% by weight of methanol and has been superheated by 10° C. are fed in at the lower end of the reaction zone ($K_1RZ$).

38% (377.7 kg/h) of the liquid (10) running down from the enrichment section are fed to the upper section of the feed side ($K_1TLO$). The remaining liquid (11) is fed in at the upper end of the offtake side ($K_1TRO$).

A temperature of 230° C. is set in the bottom of the column, with a kettle-type vaporizer being used as bottom vaporizer ($K_1E_1$). Heating steam (40 bara) is used as heating medium.

The vapour leaving the stripping section is uniformly distributed over feed side and offtake side.

The distillate (3) is taken off exclusively in gaseous form. 32.7 kg/h of a gaseous distillate stream comprising 74% by weight of methanol and 25.8% by weight of dimethyl carbonate are obtained. The azeotropic composition at the operating pressure indicated is 76% by weight.

In the side stream (5), 470.8 kg/h comprising 93.9% by weight of dimethyl carbonate, 5.9% by weight of phenol and 0.2% by weight of methanol are taken off as liquid.

The bottom product from the side stream stripper (K9) has a methanol content of less than 0.2% by weight and is mixed with a further dimethyl carbonate stream (2) having a flow rate of 59 kg/h, a dimethyl carbonate content of 99.9% and a methanol content of 0.1% by weight, vaporized, superheated and recirculated to the reactive dividing wall column below the reaction zone ($K_1RZ$).

15 kg/h are taken off in vapour form as overhead product from the side stream stripper (K9) and recirculated to the reactive dividing wall column above the side stream offtake (5).

435.7 kg/h of a mixture (6) comprising 65.2% by weight phenol, 18.84% by weight of methyl phenyl carbonate, 4.6% by weight of diphenyl carbonate, 9.94% by weight of dimethyl carbonate, 0.01% by weight of anisole and 1.41% by weight of titanium tetraphenoxide are obtained as bottom product from the reaction column K1.

The gaseous distillate is fed to a membrane separation (M) by means of pervaporation. 12.5 kg/h of a gaseous stream comprising 40% by weight of methanol are obtained as retentate and are, after condensation, fed into the upper third of the enrichment section ($K_1VT$) of the reactive dividing wall column.

A methanol-rich fraction (17) comprising 95% by weight of methanol is obtained as permeate.

The invention claimed is:

1. A process for preparing an alkyl aryl carbonate and/or a diaryl carbonate comprising reacting a dialkyl carbonate and an aromatic hydroxy compound in the presence of a catalyst in a reactive distillation column, wherein said reactive distillation column is divided by one or more separation devices which are effective in the longitudinal direction and completely or partially prevent transverse mixing of liquid and/or vapour streams into a feed side (Z) in which a reaction zone is located and an offtake side (E), wherein a stream (21) comprising said aromatic hydroxy compound and a stream (22) comprising said dialkyl carbonate are fed to said feed side (Z) and at the same time one or more middle-boiling fractions which optionally comprise reactants and/or reaction products are removed in gaseous or liquid form from the offtake side (E).

2. The process of claim 1, wherein said one or more separation devices completely prevent transverse mixing of liquid and/or vapour streams.

3. The process of claim 1, wherein said stream (21) is fed above said reaction zone and stream (22) is fed below said reaction zone.

4. The process of claim 1, wherein said aromatic hydroxy compound is phenol, said dialkyl carbonate is dimethyl carbonate or diethyl carbonate, and said diaryl carbonate is diphenyl carbonate.

5. The process of claim 1, wherein said reaction is homogeneously catalyzed.

6. The process of claim 1, wherein said stream (21) comprises said catalyst.

7. The process of claim 1, wherein said stream (21) and/or said stream (22) containing the dialkyl carbonate are fed in gaseous or heated form.

8. The process of claim 1, wherein said stream (21) is introduced in liquid form or with only a small proportion of vapour and said stream (22) is fed in gaseous or superheated form.

9. The process of claim 1, wherein at least one further section (K1TLO) which comprises no catalyst or a maximum of 1% by weight of catalyst is present on the feed side (Z) above said reaction zone.

10. The process of claim 9, wherein said section K1TLO is equipped with at least one intermediate condenser and the heat of condensation obtained by condensation in said condenser is returned either directly or indirectly to the process.

11. The process of claim 1, wherein at least one further section (K1TLU) is present on the feed side (Z) below the reaction zone.

12. The process of claim 11, wherein said section K1TLU is equipped with at least one intermediate condenser.

13. The process of claim 10, wherein said at least one intermediate condenser is integrated into said reactive distillation column or present as a separate intermediate condenser outside said reactive distillation column.

14. The process of claim 12, wherein said at least one intermediate condenser is integrated into said reactive distillation column or present as a separate intermediate condenser outside said reactive distillation column.

15. The process of claim 1, wherein said reaction is carried out at a temperature in the range of from 100 to 300° C. and a pressure in the range of from 0.5 to 20 bar.

16. The process of claim 1, wherein the reaction zone comprises from 5 to 100 theoretical plates, wherein the reaction is carried out at a temperature in the range of from 180 to 245° C. and a pressure in the range from 2 to 10 bar.

* * * * *